United States Patent [19]

Neumann et al.

[11] 4,409,652

[45] Oct. 11, 1983

[54] APPARATUS FOR PROCESSING DIGITAL SIGNALS

[75] Inventors: Leopold Neumann, Lexington; Richard B. Kline, II, Stoneham, both of Mass.

[73] Assignee: Siemens AG, Munich, Fed. Rep. of Germany

[21] Appl. No.: 186,764

[22] Filed: Sep. 12, 1980

[51] Int. Cl.³ ............... G06F 15/16; G06F 15/20; G06F 11/00
[52] U.S. Cl. ................................................ 364/200
[58] Field of Search .............................. 364/200 MS

[56] References Cited

U.S. PATENT DOCUMENTS

| | | | |
|---|---|---|---|
| 3,534,338 | 10/1970 | Christensen et al. | 364/200 |
| 3,588,881 | 6/1971 | Gordon | 340/347 R |
| 4,096,567 | 6/1978 | Millard et al. | 364/200 |
| 4,110,823 | 8/1978 | Cronshaw et al. | 364/200 |
| 4,145,739 | 3/1979 | Dunning et al. | 364/200 |
| 4,156,904 | 5/1979 | Minowa et al. | 364/200 |
| 4,236,086 | 11/1980 | Hoebel | 340/825.34 |

FOREIGN PATENT DOCUMENTS 2757783  8/1979  Fed. Rep. of Germany ...... 307/149

OTHER PUBLICATIONS

Brochure "Models 78341A/78342A Monitors–Patient Monitoring", 1978, Hewlett-Packard, Medical Products Grp., Waltham, Mass.

Primary Examiner—Harvey L. Springborn
Attorney, Agent, or Firm—Karl F. Milde, Jr.

[57] ABSTRACT

The apparatus contains a microprocessor circuit, which comprises a preprocessor which is not DMA-capable in itself and a DMA-capable central processor. Both processors can be made to communicate with each other by means of a main memory. This is performed by temporarily cutting off the communication path between said DMA-capable central processor and said main memory, specifically by an artificial DMA request via the address line of said preprocessor, and by establishing instead a communication path between said preprocessor and said main memory. The communication of said preprocessor with said main memory is started after said central processor has sent a return message signal to said preprocessor, whereby it confirms that its own communication with said main memory is completed.

12 Claims, 18 Drawing Figures

APPARATUS FOR PROCESSING DIGITAL SIGNALS

FIELD OF THE INVENTION

The invention relates to an apparatus for processing signals occurring in digital form with the use of a microprocessor circuit.

SUMMARY OF THE INVENTION

1. Objects

It is an object of this invention to provide an apparatus which, with a minimum of technical circuitry, makes possible processing of digital signals in a great diversity of forms and practically error-free.

It is another object of this invention to provide such an apparatus with the aid of microprocessors.

It is still another object of this invention to provide an apparatus which contains a preprocessor and a central processor having different tasks.

2. Summary

According to this invention, the apparatus for processing digital signals contains a preprocessor, not DMA-capable in itself, and a DMA-capable central processor having a main memory. The preprocessor and the central processor can communicate with each other by means of the main memory. This is performed by temporarily cutting off the communication path between the DMA-capable central processor and the main memory, specifically by an artificial DMA request via the address line of the preprocessor, and establishing instead a communication path between the preprocessor with the main memory. Communication via this path, however, is taken up only after the central processor has sent a return message signal or DMA-enable signal to the preprocessor, whereby it confirms that its own communication with the main memory is completed or finished.

By the term DMA-capable is understood that the respective microprocessor has its own direct access to a memory (Direct Memory Access).

According to this invention, a specific workload distribution between the preprocessor and the central is chosen. The preprocessor is not DMA-capable in itself, but is made DMA-capable by a simple circuit design which adds little to the cost of the microprocessor circuit, whereas the central processor is DMA-capable. The preprocessor, simple in design and relatively inexpensive, takes over the data preprocessing, in particular data scaling and data reduction. If necessary, it also carries out simple control operations in handling the data between a data transmitter and a data receiver. The DMA-capable and hence much more versatile central processor is relieved. It can be used more intensively for processing and control purposes of a higher order, resulting in a higher efficiency of the circuit at relatively low total costs. Moreover, the invention always ensures an unambiguous separation of the central processor and the preprocessor as far as their individual communication with the shared main memory is concerned. The mutual data traffic is not disturbed. Hence, the apparatus operates practically always error-free.

The foregoing and other objects, features and advantages of the invention will be apparent from the following more particular description of preferred embodiments of the invention, as illustrated in the accompanying drawings.

DETAILED DESCRIPTION OF THE PREFERRED EMBODIMENTS

Figure 1:
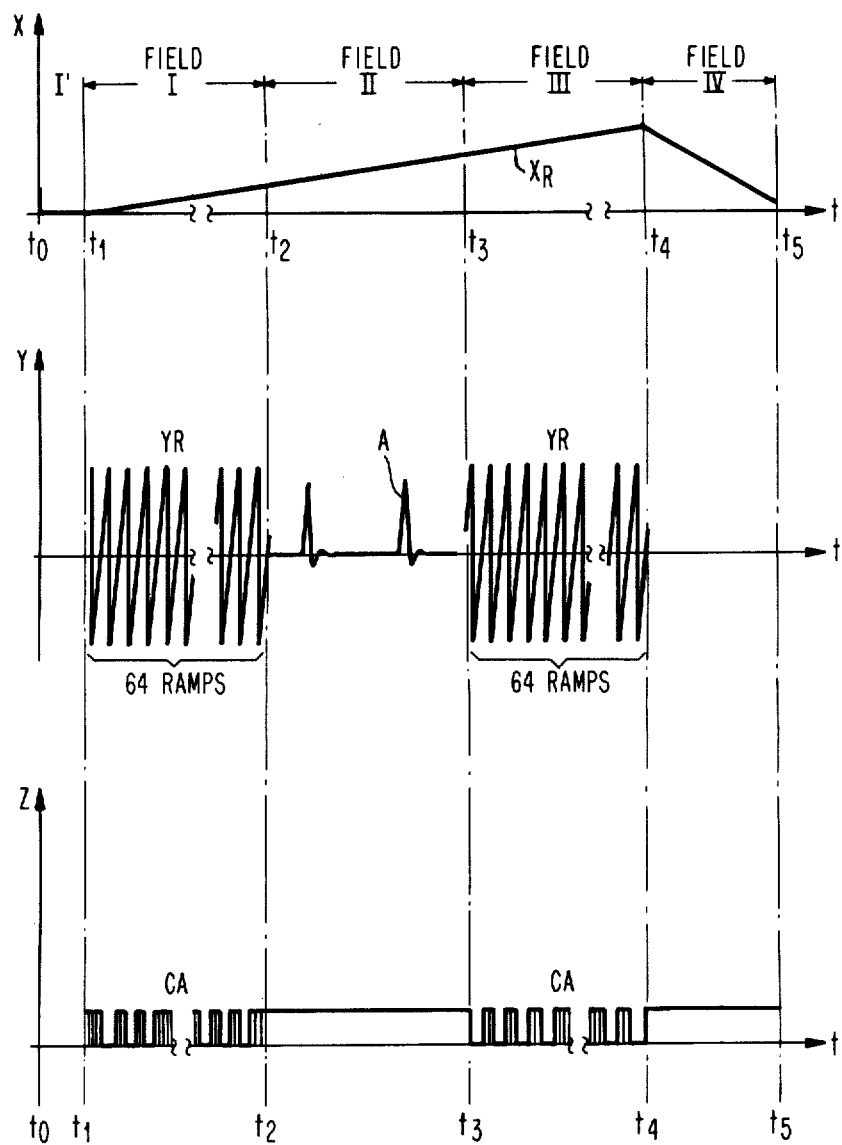
FIG. 1 is a flow chart of three coordinate signals x, y, z in varying signal conditions.

In FIG. 1 there are shown three coordinate data or signals x(t), y(t), z(t) for a signal period or sweep as a function of time t one above the other. Each coordinate curve is divided into five sections or intervals I', I, II, III, and IV. These time intervals are indicated by ordinates and dash-dot lines at times $t_0$, $t_1$, $t_2$, $t_3$, $t_4$, $t_5$. The first section I' serves for the transmission of a configuration word to be described more fully later and the device-actuation of x-reset, followed by the activation of an x-deflection. Section IV is the retrace time, also explained more fully later, of the x-deflection of an electron beam of an x,y,z oscilloscope in the respective equipment. Sections I, II, III are the main sections for the recording of alphanumerical symbols and of analog signals. They will be termed in the following also as fields for analog or symbol representation. According to the diagram of FIG. 1, therefore, the x-deflection with the ramp voltage $X_R$ begins at time $t_1$. After transmission of the configuration word in Section I', a rapid y-raster $Y_R$ follows at time $t_1$. This raster is the basis for a symbol representation. The two quantities x and y, being ramp voltages, are in field I system-specific constants which can be produced in the equipment itself. An independent transmission of such rasters to the individual equipment via a common signal line (signal bus) is thus obviated. It suffices to transmit the start (synchronizing) signals needed for the activation of the ramp voltages $X_R$ and $Y_R$ in the form of an x-synchronization signal or respectively a y-configuration signal. The presence of two system-constant coordinates x, y in field I can, however, be utilized to transmit via a common signal line (signal bus) address signals for a symbol generator contained in the respective equipment. Due to these address signals, which are transmitted in digital form, the character generator generates in the respective activated equipment unblanking signals which, in synchronism with the rapid y-symbol raster produced simultaneously in the equipment, are combined to form the desired alphanumerical symbol on the picture screen of an x,y,z oscilloscope. The address signals to be transmitted in data section I for the symbol generator are indicated in FIG. 1 for the coordinate z as digital signals CA (Character Addresses).

A significant property of section 1 (Field I) is, therefore, that the coordinates x and y are system-specifically constant, while the coordinate z is system-extraneous and variable. However, since two coordinate quantities are constants, the third variable quantity z can be generated from a single data field transmitted via the common signal line to the respective equipment.

In data section II (or Field II) of the diagram of FIG. 1, a different situation prevails. The y-coordinate transmission section of an analog signal A (e.g., EKG) is now system-extraneous and variable. Hence, in the case of Field II, the coordinate y is not a system-specific constant quantity; to be able to transmit only this quantity A, it is necessary that, in addition to the x-coordinate in field II, also the z-coordinate must be system-specific and constant. And so it is, for according to the diagram of FIG. 1, the z-coordinate shows in data section II, a constant voltage curve (continuously intensified, except for a blanking bar as explained later).

Concerning field III, there are two possibilities: on the one hand, if necessary, the signal curve as obtained for field II can be continued for all three coordinates x, y, z. Accordingly, in field III, at constant voltage of the z-coordinate, the analog quantity A would continuously be transmitted in the signal path as y-component.

On the other hand, it is possible to switch back to reproduction according to the pattern of field I. In this case, therefore, there is again produced in field III, with respect to the y-coordinate, solely by a device-generated signal, a rapid y-deflection raster $Y_R$ for symbol representation, and in the signal path to the equipments again address signals CA for correct addressing in the symbol generator are transmitted during this time span as codes for the device-generated z-component.

The representation of FIG. 1 is merely an example. Naturally the individual fields I to III can be lined up in any desired variable way. Also, the total number of fields can be other than three. In different fields, analog signals can selectively be represented together with symbols. Or only analog signals or only symbols may be reproduced in a single track. As has been indicated above, the section I' preceding the main fields I to III may be used solely for the transmission of a sweep-configuration signal. It is again a matter of course that in this section still other command signals of any kind may be transmitted in addition to the configuration signal. Alternately, such supplementary signals may, as has also been indicated above, be placed into those phases (e.g., fields I and/or III) in which rapid y-rasters are produced for symbol representation. The supplementary command signals are then transmitted via the common signal path together with the digital address signals CA in appropriately mixed form. Moreover, such supplementary signals can be transmitted also in phase IV, that is, in the retrace phase of the electron beam after an x-deflection.

Figure 2:
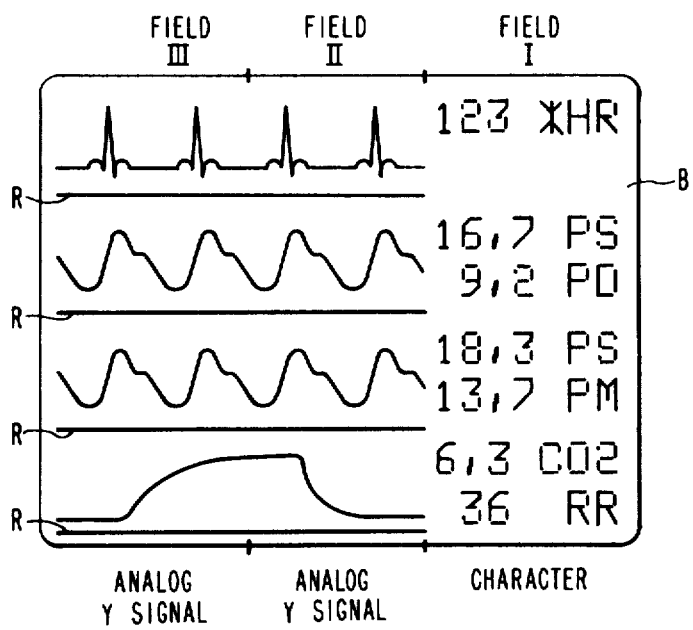
FIG. 2 is a display of analog signals and character signals on the image screen of an x, y, z-oscilloscope.
Figure 3:
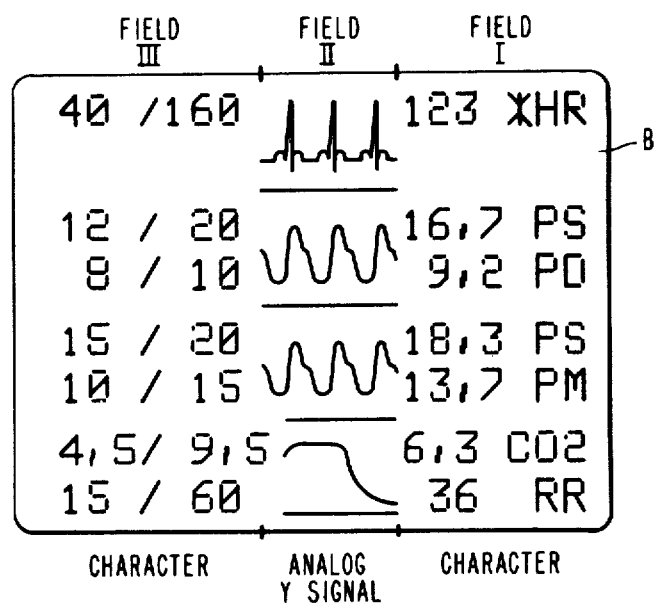
FIG. 3 is a similar display additionally showing limit values.

The combination of the various data sections of analog signals and symbols results in a total picture on the picture screen on an x,y,z oscilloscope is shown by way of example in FIGS. 2 and 3. Here the picture screen of the oscilloscope is marked B. It is seen at once that both in FIG. 2 and in FIG. 3 alphanumerical symbols are represented in field I on picture screen B. In field II are recorded sections of an analog signal A. In FIG. 2, the recording of this analog signal is continued in field II. In FIG. 3, alphanumerical symbols in the form of limit values (limits) are gated in field III.

In the oscilloscopes of FIGS. 2 and 3, the beam deflection of the electron beam for signal recording is from right to left viewing from in front on screen B. On the right side of screen B, therefore, alphanumerical symbols always appear first in field I. Then follows field II with the representation of an analog signal. Field III can then be utilized either to continue the recording of the analog signal (FIG. 2) or for again gating in alphanumerical symbols (FIG. 3).

It can be seen from FIGS. 2 and 3 also that the oscilloscopes shown are, for example, four-channel oscilloscopes. Although, the invention is also applicable to any number of channels, particularly one or two. Thus, the manner in which these oscilloscopes operate is that, in time succession, in channels stacked one below the other, up to four different analog signals with respectively correlated symbols can be represented. In each symbol field I and/or III, by suitable stacked address selection in the symbol generator, one or more lines of symbols per channel (e.g., as shown up to two lines of symbols) can be correlated with a single signal curve simultaneously. In the present embodiments of FIGS. 2 and 3, there are thus represented on the picture screen of the respective four-channel oscilloscope in channel 1, e.g., the EKG of a patient together with symbols which indicate for both figures in column I, e.g., the value of the heart rate (frequency) and for FIG. 3 in column III specifically further an upper and a lower limit value of the heart (rate) frequency. In the channels 2 and 3, instead, there are represented, for example, two blood pressure curves. The symbols gated in fields I of both figures are data indicating the respective blood pressure value of the systole, diastole, or mean pressure. The symbols reproduced in field III of FIG. 3 are again limit data for the blood pressure values. Channel 4 lastly shows the curve of the $CO_2$ content in the patient's respiration gas, and measured parameters and limits for the $CO_2$ content. Thus, in the diagram there are to be correlated to the analog signals either only purely quantitative data or, additionally, limit value data about maximum or minimum critical limit values of the physiological test signals in the form of alphanumerical symbols. By adding limit value data, limit value exceedings, and hence, also critical developments of a physiological parameter, can be recognized at once. In the present case, critical limit value excesses are further indicated by giving an alarm signal (in particular, an audible and/or a visual alarm). If, in the basic equipment, the picture content of a trend memory is represented, the analog curves shown in FIGS. 2 and 3 are replaced accordingly by trend curves.

For the quality of the system to be displayed, it is essential that the image representation of all signals to be displayed is flicker-free. To ensure absence of flicker, a 50 Hz or greater frame frequency is desirable. Accordingly the total time of the beam deflection over the picture screen of the respective oscilloscope is 20 ms. If recording in four channels is desired, the total deflection time, including flyback (retrace) may thus be at most 5 ms per channel.

Figure 4:
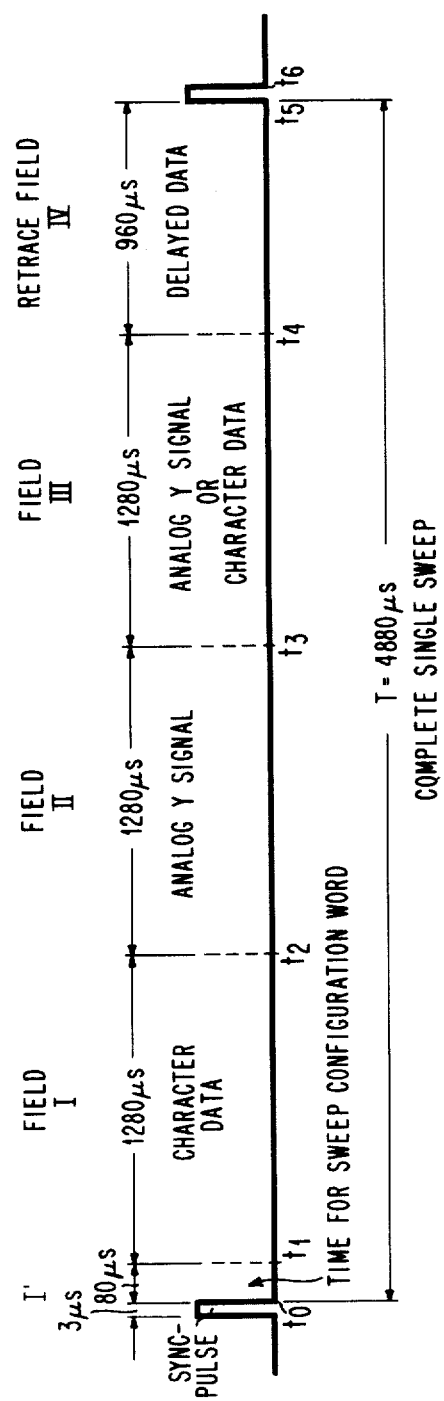
FIG. 4 is a diagram of a complete sweep.

FIG. 4 shows a time plan for signal transmission adapted in this sense. In the time plan of FIG. 4, the total duration T of an x-deflection is stated as $T=4,883$ $\mu s$. This duration T is divided into a total of five times sections I', I, II, III, IV. As has been mentioned before, in the beginning a synchronizing pulse SP (3 volt, 3 $\mu s$) at time $t_0$ fixes the beginning of the time duration, e.g., by its falling edge. The control of all equipments involved by the synchronizing pulse of a single equipment snychronizes all other equipments with one another, unless a synchronizing pulse is impressed on all other equipments by an external central unit from the start. After the syncrhonizing pulse SP comes first the time interval I', which in the present case is 80 $\mu s$ long.

During this time interval I', which ends at time $t_1$, there is conveyed to all equipments the display configuration for the full x sweep deflection configuration signal (8-bit sweep configuration word) as a digital signal, which serves as a coded signal as to how the beginning and/or end as well as the manner and location of the instantaneous y-representation on the screen of the oscilloscope must be selected in comparison with the signal representation to be transmitted to another equipment. The deflection configuration signal can be defined as follows as an 8-bit word, BIT 0 to BIT 7, for the present embodiment in application to a four-channel oscilloscope:

| BITS | | DESCRIPTION |
|---|---|---|
| Bit 0 | (LSB) | Field III Control |
| | | Zero = Analog Display (+0.75V in CV) |
| | | One = Character Display (−1.0V in CV) |
| Bit 1: | BOT 0 | These bits control the vertical location of the bottom (BOT) of the trace for the Analog |
| Bit 2: | BOT 1 | parameter display per table below. |
| BOT 1 | BOT 0 | |
| 0 | 0 | Bottom position |
| 0 | 1 | Middle Lower Position |
| 1 | 0 | Middle Upper Position |
| 1 | 1 | Top Position |
| Bit 3: | RT 0 | These bits control the vertical locaton of the character display and the retrace line (RT). |
| Bit 4: | RT 1 | These bits also identify the trace. They are codes as follows: |
| RT 1 | RT 0 | |
| 0 | 0 | Channel 4 Bottom |

| BITS | | DESCRIPTION |
|---|---|---|
| 0 | 1 | Channel 3 |
| 1 | 0 | Channel 2 |
| 1 | 1 | Channel 1 Top |
| Bit 5: | G 0 | These bits control the Y deflection gain (G) |
| Bit 6: | G 1 | for analog waveforms per table below: |
| G 1 | G 0 | |
| 0 | 0 | Gain = 3 (Expanded Pressure) |
| 0 | 1 | Gain = 2 (Expanded Pressure) |
| 1 | 0 | Gain = 1 Normal |
| 1 | 1 | Gain = 0 and Blank |
| Bit 7 | | Retrace intensify. The retrace line in the position defind by RT0, RT1 will be intensified if the bit is a one. |

Following section I' comes the first field I. The duration of this field is 1280 $\mu s$. Field II, which is also 1280 $\mu s$ long, follows after Field I at time $t_2$. Field II is followed at time $t_3$ by field III, which also lasts 1280 $\mu s$. Then the x-deflection is terminated by the section IV, which is 960 $\mu s$ long and which fixes the retrace time for the electron beam. In the signal display of FIGS. 2 and 3, the retraced electron beam is gated in as a thin trace R in the picture plot by special selection in the configuration word. The retrace line R signals the location of a reference or zero line in each channel. The retrace phase IV interval for the electron beam can be utilized for the transmission of any additional command signals. Also, cyclically revolving memory values or data of the analog signals can be removed during the retrace time from the picture repeating memory and be supplied for example to a co-running printer, recorder or the like, as so-called delayed data. These signals may be transmitted during the retrace time, either synchronously or, preferably, asynchronously.

Moreover, if necessary, during phase IV, data may be rearranged in memories in any manner or erased. The end of the retrace phase IV is at the same time the beginning of a new deflection period. Thus, at time $t_5$, a new synchronizing pulse SP is generated which, after switching to the next following channel of an oscilloscope, triggers the electron beam with its falling edge at time $t_6=t_0$ for the next time interval. The triggering always occurs in such a way that the electron beam of the oscilloscope, regardless of where it happens to be on the picture screen in the retrace phase, is immediately pulled back (reset) to its initial position in the right outer edge position of the screen. The momentary instability resulting due to the abrupt interruption of the retrace phase is bridged by the time interval I' following the sync pulse with transmission of a configuration signal, which, of course, is not itself reproduced on the screen.

The invention is employed in particular in medicine in picking up physiological signals, as in particular ECG, blood pressure, temperature, $CO_2$, etc., on the body of a patient. A single device of this kind is illustrated, for example, in FIG. 5 in the basic circuit diagram. This device comprises a total of four replaceable modules 1 to 4, to receive and transfer picked-up physiological signals to a module coupling and control unit 5. This unit 5 has a power coupling with each single slide-in module 1 to 4 via a pair of coils 6 and 7 for each module. These coils transfer the energy required for the operation of the slide-in modules from unit 5 to modules 1 to 4. The transfer of the physiological signals or other received signals from a slide-in module to unit 5 occurs by means of optocouplers 8, 9. Symbol 8 indicates an emitting diode, in particular, an infrared luminescent diode. Symbol 9 indicates a light receiver, in particular, a photo diode. For the transmission of signals, e.g., switching signals, A/D clock signals, or other control signals from unit 5 to a slide-in module 1 to 4, a further optocoupler 10, 11 is provided. This optocoupler therefore has a transmitting diode 10 at unit 5 and a receiving photo diode at the respective module 1 to 4. Further details concerning the internal basic circuitry of a module 1 to 4, as well as of the module coupling and control unit 5, can be seen from the description relating to FIGS. 13 to 15 following below.

Figure 5:
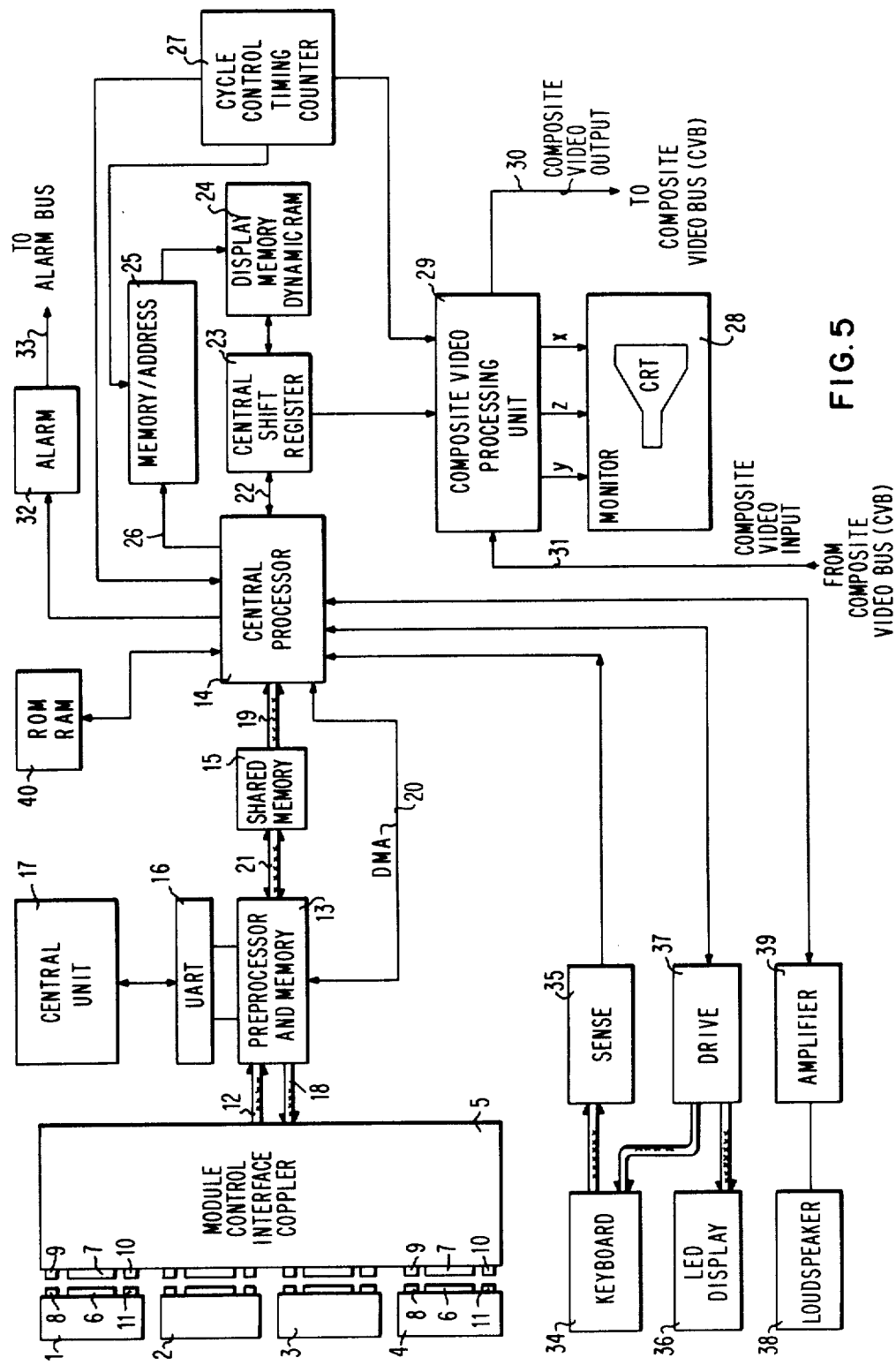
FIG. 5 is a basic circuit diagram of an electromedical monitoring device.

As a practical realization of the arrangement (cf. FIG. 12), the equipment comprises in the equipment housing a bay into which the slide-in modules 1 to 4 can be introduced one above the other in levels. The bay comprises a rear wall on which is mounted the unit 5 with the first half-parts of the respective power coupling transformer and respectively, the optocoupler. The other half-part of the power coupling transformer and optocoupler is arranged as indicated in FIG. 5, on the back of the respective slide-in module 1 to 4. So, if the slide-in module is fully inserted into the bay of the equipment housing end position, the half-parts of the coupling transformer carried by it align with the half-parts of the back wall to a complete non-galvanic coupling point for power, and signal transmission. The unit so assembled is ready for operation.

The physiological or other signals picked up by unit 5 are now fed via a path (data arrow) 12 to a microprocessor 13 for data preprocessing (Preprocessor), in particular, data scaling and data filtering (weighting). As will be explained more fully in the description relating to FIG. 16, this microprocessor transfers the preprocessed data to a central microprocessor 14 via a common addressable part of a main memory 15 (shared memory) with the aid of a special hardware circuit which permits direct access DMA to memory positions (DMA = Direct Memory Access). In addition, the preprocessing microprocessor 13 comprises an On-Chip UART 16 (UART = Universal Asynchronous Receiver Transmitter) for communication with a central station 17. The preprocessor 13 can transmit moreover, as indicated by data arrow 18, signal data such as clock signals, configuration signals, or the like, via unit 5 as part of the combined signal in the signal path via the optocouplers 10, 11 to the individual slide-in modules 1 to 4. Memory 15 is normally associated first with the central microprocessor 14 (data arrow 19). During the use of the shared memory by the Central Processor, the preprocessing microprocessor 13 is isolated from the shared memory. Upon DMA request by the preprocessing processor (line 20), the central microprocessor 14 is temporarily disconnected from memory 15, and the preprocessing processor 13 takes over the access to the shared memory 15 via the memory data arrow 21.

The central microprocessor 14 is the essential part of the apparatus. By it, via a data line 22, the occurring signal data are read via a central shift register 23 into a dynamic RAM 24 under the control of an address counter 25 which receives address data from the center microprocessor 14 via an address line 26. The central shift register 23 receives all occurring data in parallel formation and reads them out again serially. The time sequence of the reading in and out of data is controlled by a central clock generator 27 (Cycle Control Timing Counter). The data to be forwarded from RAM 24 to oscilloscope 28 for recording are preprocessed in a processing device 29 and then sent to the oscilloscope. Device 29 comprises all structural elements required for the generation or, respectively, for the forwarding of the sensation-wise (sic) signal train (composite video signal) according to FIG. 1. By device 29, therefore, signals and symbols corresponding to the FIGS. 1 to 4 are developed and supplied to the equipment-specific monitor 28. At the same time, all signals developed in this sense are sent also via an output 30 (composite video output) to a transmission line common to all equipments of any desired equipment configuration (composite video bus). Moreover, the device 29 comprises also a corresponding input 31 (composite video input) through which the equipment is likewise connectable to the common connecting line for all devices. Thence, in case of need, e.g., in case of an alarm, while switching off its own locally-generated data flow to the oscilloscope, composite video signals can be introduced from any desired other device, in particular that of the alarm instance, from the common transmission path for displaying on the equipment-specific oscilloscope 28. The alarm is set off by an alarm device 32 connected to the central microprocessor 14 and sent, e.g., in arrow direction 33 to an alarm bus. For the input of special command data into the central processor 14 there serves a bank of keys 34, e.g., on the front panel of the respective device, with sensor 35 for correct input. For the display of data entered or occurring during signal processing, there serves an LED display 36 (luminescence diodes) with driver stage 37. A loudspeaker 38 with amplifier 39 serves for acoustic signal indication, e.g., for alarm, for key click of the keys of a bank of keys or respectively, "beep" tones for occurring QRS pules or also indication of an interrupted program of the central processor. Component 40 is a ROM and RAM supplementary memory for the central microprocessor.

Figure 6:
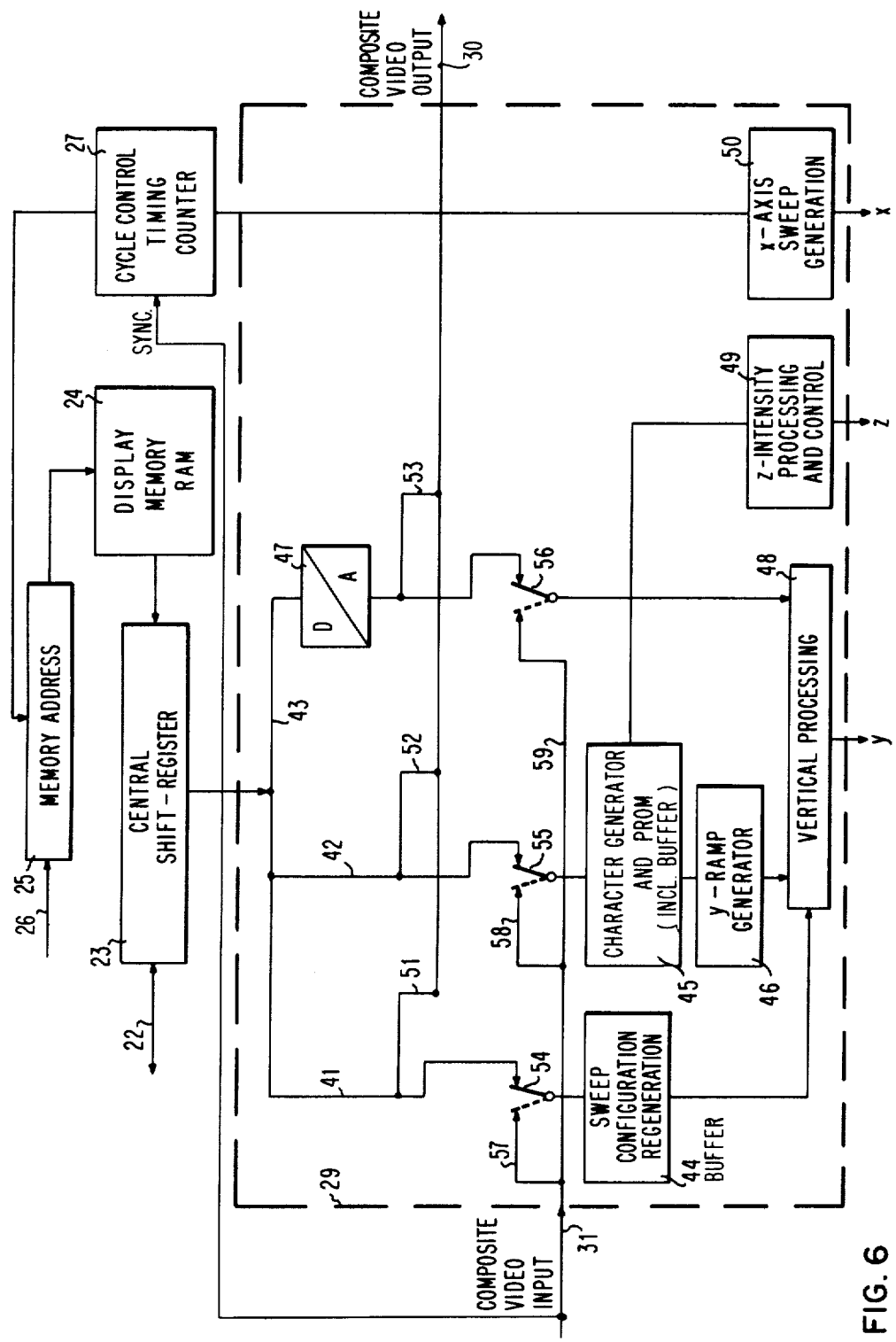
FIG. 6 is the basic circuit diagram showing details of the monitoring device according to FIG. 5.

The device for the generation and forwarding or also reception of composite video signals is shown in detail in the basic diagram of FIG. 6 as a component, e.g., of an equipment according to FIG. 5. According to it, the output of the central shift register 23 branches within signal processing device 29 into at least three signal paths 41, 42, and 43. In each of these signal paths, a specific signal processing member is inserted. Thus, in signal path 41, there is a decoder 44 for the y-configuration word. In signal path 42 are on the other hand located the character generator 45 for character formation (local ROM for 2×7 character dislay in 8-bit code) and the ramp generator 46 for generation of the rapid y-deflection raster (y-ramp voltage $Y_R$). In signal path 43, lastly, the digital-to-analog converter 47 for generation of the analog signals A is inserted. The outputs of decoder 44 for the y-configuration signal of generator 46 for the y-deflection raster and of the digital-to-analog converter 47, lead to a system 48 for the processing of all incoming signals to the vertical deflection signal y for the display-connected oscilloscope 28. The character generator 45 has a further output to the unblanking system 49 of the oscilloscope, which furnishes the unblanking pulses needed for character construction. For the x-deflection, an x-ramp generator 50 is provided, which is triggered directly by the internal clock generator 27 of the equipment via the sync pulses SP.

The described signal path is the path for such composite video signal as the equipment generates itself. For the forwarding of this self-generated signal there serves, as previously mentioned, an additional equipment output 30 (composite video output) which leads to a composite video bus common to all equipments. In FIG. 6, this additional signal path is marked by taps 51, 52, and 53. Taps 51 and 52 are present at the signal paths 41 and 42 before switches 54 and 55, which are connected ahead of the decoder 44 for the y-configuration signal and of the character generator 45. Tap 53 at signal path 43, instead, lies at the output of the digital-to-analog converter 47 before a switch 56. The switches 54 to 56 normally connect the signal paths 41, 42, and 43 directly with the system-specific image generators 44 to 49. However, they have also a second switching position (shown by dashes) in which they can be switched in the manner shown to the signal paths 57, 58, and 59 of the composite video input 31. Upon switching to input 31, the signal supply from the system-specific signal generator 23, 24 to the structural elements 44 to 49 is thus interrupted. Instead of the locally-generated composite video signal, there is now applied to the oscilloscope the composite video signal of an external (in particular, alarm-giving) equipment. Simultaneously, however, the system-specific composite video signal continues to be supplied to the composite video output 30 unhindered thereby.

Figure 7:
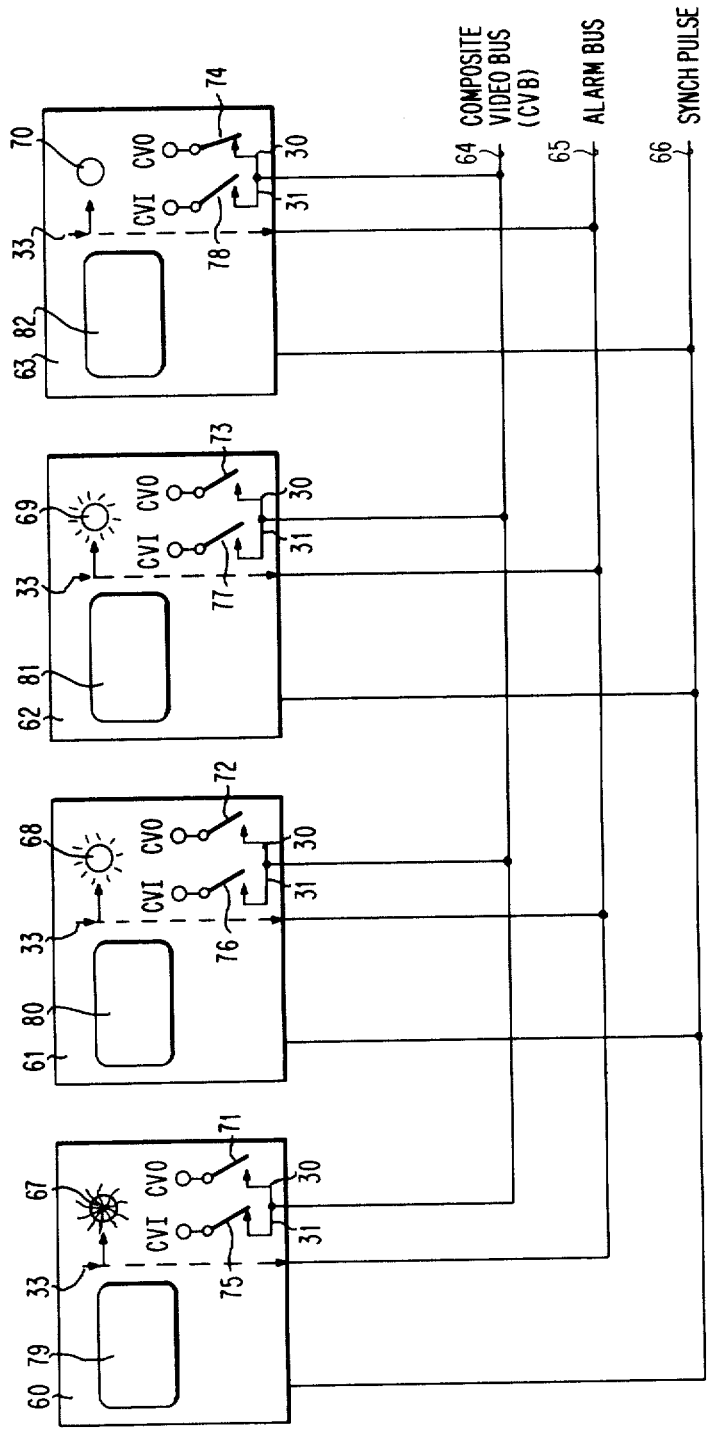
FIG. 7 is an arrangement of individual monitoring devices in series connection without a common central unit.

FIG. 7 shows a typical application of the invention comprising a chain of individual monitoring devices having no central unit. Here are shown, for example, a total of four bedside devices 60 to 63, each of which is constructed and generates a composite video signal as has been described in the explanations regarding the preceding FIGS. 5 and 6. All four devices of this chain (the number of devices can be increased as desired) are interconnected via a total of three lines 64, 65, 66 (or respectively connectable via switches, as will be later explained in more detail). Thus, e.g., line 64 is the common signal bus (CVB) for the composite video signal (CV). Line 65 is the common alarm bus and line 66 finally is the common transmission line for the sync pulse SP for synchronization of the x-deflection timing of all devices 60 to 63. Each of the devices carries on the front (indicated schematically) a LED key 67 to 70.

In each of these keys, therefore, a luminescence diode (LED) is integrated. Each of the luminescence diodes in turn is in circuit connection with the alarm bus 65 such that it lights up inside the key when an alarm signal is generated and put out on the alarm bus by another device of the chain. In the alarm-giving device itself, however, the LED there is not activated. Here the alarm situation is indicated visually and audibly by separate indication means. The doctor or the monitoring nurse can then immediately distinguish whether the respective device itself gives the alarm, i.e., whether the patient connected to it is himself the alarm patient, or whether another device of the chain containing the connected patient is the subject of the alarm.

As to the transmission of composite video signals from the devices 60 to 63 to the composite video bus 64 or respectively, the receipt of such signals from the composite video bus 64 by individual devices, there are inserted in FIG. 7 inside the blocks which symbolize the devices 60 to 63, symbolic switches 71 to 78. The switches 71 to 74 (CVO switches) are inserted in the lines 30 (see FIGS. 5 and 6) of the video signal outputs (CVO) of the devices. The switches 75 to 78 (CVI switches) are inserted in the lines 31 (see FIGS. 5 and 6) of the video signal inputs (CVI). A closed CVO switch 71 to 74 thus means that the respective device 60, 61, 62, or 63 specifically feeds its composite video signal, which at that moment it also simultaneously projects on the picture screen of its own oscilloscope 79, 80, 81 or 82, into the composite video bus 64. A closed CVI switch 75 to 78 means that the composite video signal currently being fed by another device into the composite video bus 64 is taken over by the respective device via the video signal input thereof from the CV bus and is reproduced on the picture screen of the oscilloscope 79, 80, 81 or 82 of this device rather than reproduce its own composite video signal.

In the embodiment of FIG. 7, e.g., device 63 gives alarm. This alarm is transmitted via alarm bus 65 to the devices 60, 61 and 62 (or all additional devices if such are additionally connected in the chain). Hence, the LED keys 67, 68 and 70 of these devices light up, this being indicated in FIG. 7 by symbolic light rays at the edge of the keys. According to the foregoing statements, the CVO switch 74 of device 63 had also been closed at the moment of alarm. The CVO switches 71, 72, and 73 of devices 60, 61 and 62, instead, remain open, since in these devices no alarm was produced. Accordingly, the composite video signal of the alarm-giving device 63 is fed into the composite video bus 64. This composite video signal can now be taken from the CVB 64 by any desired device 60 to 62 by pressing of one of the LED keys 67 to 69. Pressing of a flowing LED key causes the steadily lit lamp to change to blinking. It is thereby indicated that, on the picture screen of the oscilloscope of the respective device, no longer the locally generated information but a remote signal image is projected. Flashing of a key is indicated symbolically in FIG. 7 by rays which extend radially into the key center.

In the embodiment of FIG. 7, e.g., the LED key 67 of device 60 was pressed. Hence, the CVI switch 75 of this device was closed and the CV of the alarm-giving device 63 thus passes via the composite video input of device 60 into the CV-processing signal portion of this device and thence accordingly to the picture screen of oscilloscope 79.

The described switching sequences of the switches 71 to 78 are purely of an exemplifying nature. There are many desired modifications that can be employed without significantly changing the basic sequence of the CV output by a device into the CV bus or, respectively, the receipt of CV signals from the CV bus by another or several other devices. Thus, it is perfectly possible that by modifying the above described manner, e.g., via closed CVO switches, all CV signals of all devices are normally continuously fed into the CV bus. On the other hand, when an alarm signal appears in the common alarm bus, all CVO switches are opened except the CVO switch of the device which gives an alarm therefore, only the alarm-affected CV is fed into the CV bus, as desired.

In comparison with the basic circuit diagram of FIG. 6, the respective CVI switch 75, 76, 77 and 78 can symbolize the three switches 54, 55, 56. An open CVI switch of FIG. 7 would thus correspond to the first switching position of the switches 54, 55, 56 in FIG. 6, in which the equipment-specific CV generators 23, 24, etc., are connected directly with the picture-composing components 44 to 49 via the lines 41, 42, 43. A closed CVI switch of FIG. 7, would, instead, represent the second switching position, in which these direct connections are interrupted and instead the picture-composing components (except for the A/D converter 47) are connected with the signal lines 57, 58, 59 of the CVI. Alternatively, the respective CVI switch may be designed, e.g., as a supplementary control switch for the switches 54, 55, 56, which switches the switches 54, 55, 56 as soon as it is closed by depression of the LED key. In special development and independently of the above-described operational possibilities, the CVI switch may be an integral contact part of the LED key.

As to the priority of alarms, the switches are also controlled as follows: If an alarm is given by a single device, there results the above-described function sequence. But if alarm is given by two or more devices, the above-described function sequence occurs fundamentally only for that device which of all alarm-giving devices has produced an alarm first. Only for this device the respective CVO switch closes; the CVO switches of the other alarm-giving devices remain open until the alarm of the first device has been reset, e.g., by pressing of an alarm reset key. As soon as this has been done, the device which was the first to give an alarm is replaced by a next following device giving an alarm (in the case of several devices giving an alarm simultaneously, e.g., the device with the lowest bed number, then that with the next higher bed number, etc.).

It is therefore, a significant property of a chain circuit as set forth in principle in FIG. 7 that each device within the chain can assume the function of a central device which in the central function can then poll any desired other device which e.g. just then produces alarm the composite video signal thereof for displaying on the picture screen of its own oscilloscope. It is essential only that for the assumption of the central function a LED key be pushed at the respective device.

According to a somewhat modified principle there functions, instead, an arrangement of bedside devices for which a central unit is provided from the start for the control of the total process. Such an arrangement is shown in the basic circuit diagram of FIG. 8. In this arrangement, a central unit 83 has associated with in n signal devices (bedside units) which are connected with the central unit in star form via bedside device composite video buses for bedside device composite video signals CVB1 to CVBn and alarm buses for bedside device alarms AL 1 to AL n. A single central composite video bus (composite video central) for a central composite video signal CVC leads from the central unit back to the bedside devices. In a basic cluster configuration, preferably n=4 single devices are associated in star connection with a central unit 83. The present circuit of FIG. 8, however, contains, e.g., n=16 single devices in star connection with the central unit 83, of which, however, only the first two devices of the total 16 bedside devices are shown. These two devices are indicated by the numbers 84 and 85. The n=16 single devices may, if necessary, be divided into sub-groups (clusters) of again preferably 4×4 bedside devices. To each group there is then assigned, e.g., its own wall terminal connected to the central unit. Each of the bedside devices of the star formation with the central unit is laid out in principle and functions with respect to the generation of its CVB 1 to CVB n exactly as previously described in FIGS. 5 and 6. Blocks 86 and 87 inside the device blocks 84 and 85 thus symbolize essentially the combinations of those structural elements 41 to 56 of the picture processing and picture recording section of the devices as are represented in detail in particular in FIG. 6. Blocks 88 and 89 indicate the picture repetition memory 24 with respective shift register 23, address computer 25, clock generator 27, etc. These elements are likewise explained in principle in FIG. 6.

Also, with respect to the generating and communicating of an alarm, as to principle the same mechanisms occur as described for the chain circuit of FIG. 7. The only, but here very essential, difference is that all single devices 84, 85, etc., already have associated with them a central unit 83 which from the start and alone assumes the central function. Assumption of the central function by any bedside device, as is possible in the circuit arrangement of bedside devices in chain formation (FIG. 7), is thus not possible with the star connection. It results from this that not only are all composite video signals CVB 1 to CVB n of the single bedside devices sent to the central unit in star form via single composite video buses 90, 91 (for the first two buses), 92 (for the 16th bus); the same occurs also with alarms, as each single bedside device 84, 85 of the star formation is connected with the central unit 83 likewise in star form directly via a device-specific alarm bus. Of the sixteen alarm buses in all, the first two buses are indicated by 93, 94 and the 16th bus by 95. Thus, if an alarm is produced by one of the sixteen bedside devices 84, 85, etc., this alarm is sent to the central unit 83.

With respect to the central picture processing and picture composing section 96, the central unit itself is constructed in principle exactly like a bedside device. Like a bedside device, it comprises also a repeating memory 97 and a central microprocessor 98. Instead of slide-in modules with appropriate data traffic, however, there are inserted in the central unit appropriate auxiliary cards consisting of a central signal and data multiplexer 99, an alarm multiplexer 100, and a control device 101 for data and address control between central multiplexer 99 and central picture repeating memory 97. The central signal and data multiplexer 99 has the input lines 90, 91, etc., to 92 for the total of sixteen composite video signals CVB 1 to CVB 16 of the sixteen single bedside devices. It is connected to the output side via lines 102 to 106 for signals A, B, C, D, CH with the control system 101, which, in turn, is connected on the output side via data buses 107 and 108 as well as via address buses 109 and 110 with the central picture repeating memory 97 and the central microprocessor 98. Moreover, a further output line 111 of the central multiplexer 99 leads via a switch 112 directly to the signal input of the picture processing and picture displaying section 96 of the central unit. Via this switching line, the picture section 96 of the central unit receives the complete composite video signal CVB of a freely selectable bedside device of the star configuration. Lastly, the central multiplexer 99 has also three outputs 113, 114, and 115 for recorder signals REC 1, REC 2, REC 3, which, if needed, can be recorded on two signal recorders 116, 117 integrated in the central unit as well as on a signal recorder to be connected externally (connection arrow 118). For the synchronization of the recorders are used synchronizing signals Synch 1, Synch 2, Synch 3, which occur at output lines 119, 120, and 121 of the central multiplexer 99. The signals REC 1, REC 2, REC 3, together with the synchronizing signals Synch 1, Synch 2, Synch 3 are decoded in decoders 122, 123, 124 and then switched onto the recorders by means of switches 125, 126, 127. The alarm multiplexer 100 has an output alarm bus 128 to the central processor 98. The central processor 98 is connected to the picture section 96 of the central unit via a data and address line 129, and it is further in constant communication with the control system 101 via lines 130, 131. Another very essential component is the central composite video bus 132. Via this central bus, the composite video signal CVC of the central unit is returned to the bedside devices (or respectively also connectable to the recorders 116, 117, etc.). If necessary (again by pressing of a LED key as for chain connection according to FIG. 7), the central composite video signal can be connected from the central bus 132 to a bedside device at any time. It suffices for this operation to actuate a switch 133, 134, etc. (LED key). The CVC then becomes the composite video input into the picture processing section of the respective device. The locally generated signal image is then replaced by the central image.

It is, therefore, a significant property of the star configuration that the composite video signals CVB 1 to CVB n of the bedside devices 84, 85, etc., are connected to the central unit 83 in star form. Normally, the central unit comprises, however, likewise only one single oscilloscope with maximally four channels. Thus, it is possible to take over on the picture screen of the central oscilloscope at most the four channels of a single display device 86 or 87, etc., as selected CVB via line 111. A time-staggered switching of the central indicating device 96 to other display devices is indeed possible by the time multiplex of the multiplexer 99 and is being realized as such; but difficulties arise in the realization of a reproduction method where signals of certain channels of devices 86, 87, etc., of different bedside devices 84, 85 are to be displayed in mixed form on the central device 96. The various picture devices may operate in different bedside devices at very different display speeds of the x-deflection. Thus, there are, e.g., devices which by means of speed selectors are set for a maximum deflection speed of e.g. 50 mm/sec, and others set for the minimum deflection speed of e.g. 12.5 mm/sec. Each device can be switched at least between these two deflection velocities. The simultaneous reproduction of signal tracks with different deflection velocity is, however, practically hardly feasible.

Figure 8:
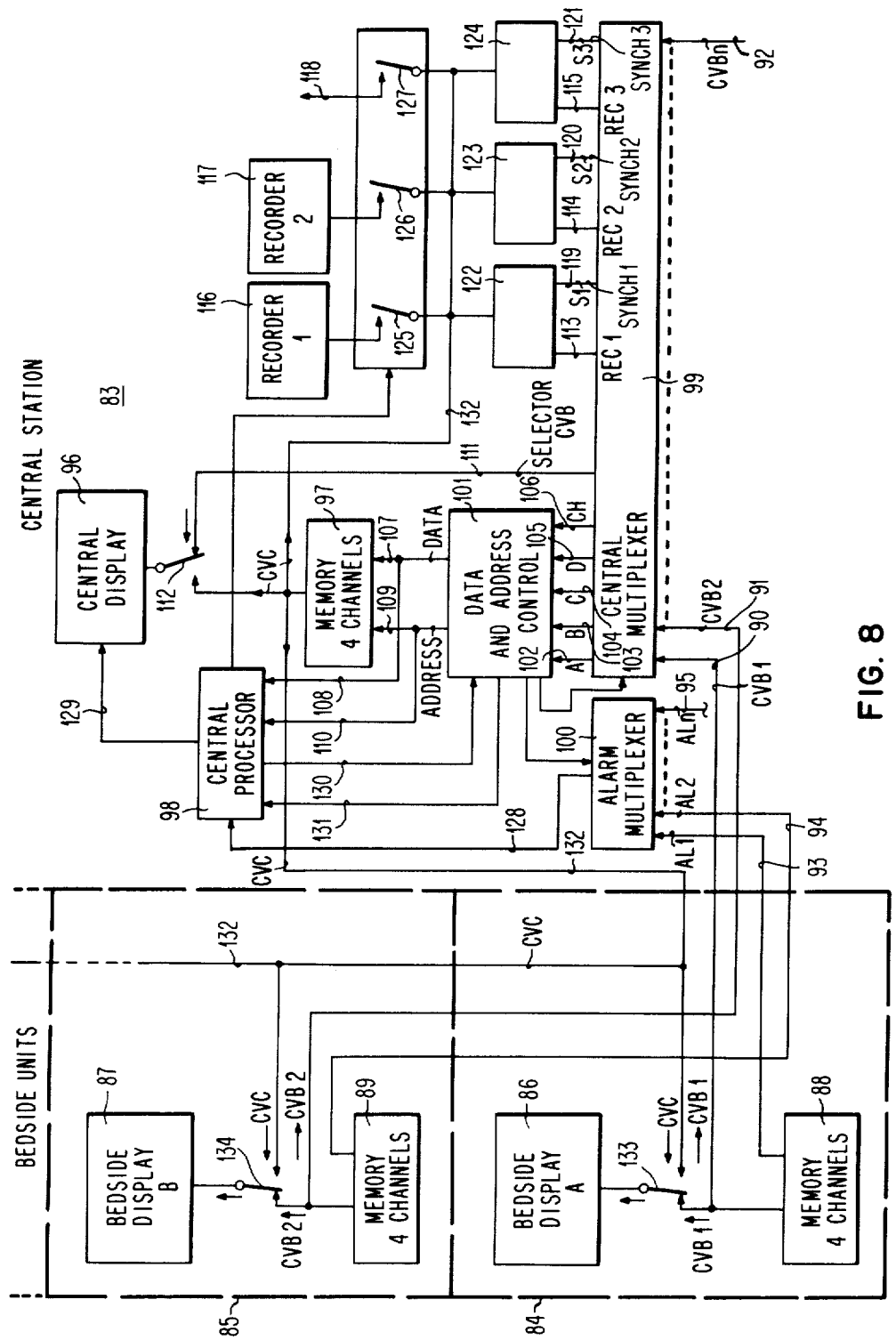
FIG. 8 is an arrangement of individual monitoring devices in star connection with regard to a common central unit.

However, the star connection of FIG. 8 also accomplishes this function, namely through a special circuit design. This design is characterized by the following aspects: The first aspect takes into account the fact that at each frame repeating memory in the picture processing section of a single bedside device, there occurs with each input of a new measured value an oldest measured value which is eliminated from the signal display. The ejection of this oldest value is now synchronized with the period of a signal display so that it falls into the retract time of the x-deflection (second aspect). The oldest measured value is thus no longer reproduced in the signal picture; it is, however, available as delayed data for reproduction on another picture device if such a delayed reproduction is desired. Now the central unit 83 in the star connection of FIG. 8 takes advantage of this circumstance (third aspect). This central unit comprises a picture repetition memory 97, which receives delayed measured values A, B, C, and D from all devices in the time multiplex via the multiplexer 99. The delayed data are registered in the picture repetition memory by the control system 101 together with the character addresses CA. Thence, they can be polled again at any time and in any mixture of the signal tracks and be displayed on the central display device 96 as mixed picture.

The described circuit makes it possible, therefore, that on a central oscilloscope inside a central station 83 having, e.g., four channels there can be displayed in any varying order a total of four different channels from oscilloscopes of four different bedside devices.

If at one of the external devices an alarm appears, this alarm passes via the corresponding alarm bus AL 1 to AL n to the alarm multiplexer 100 and then to the central processor 98. The central processor 98 now controls the signal transfer between image repitition memory 97 and display device 96 in such a way that the delayed data of the alarm-giving signal channel (e.g., alarm-giving EKG) is displayed instead of a preceding signal value record into the display channel with the highest number, i.e., into the fourth display (top to bottom) channel. If a second alarm-giving signal channel appears, it is accordingly registered in the next lower display channel, i.e., in the third channel, etc. Simultaneously with the display of the alarm-giving signal channel, the frame repeating memory repeats the number of the bed at which the alarm-giving device is installed. The bed number is visually emphasized on the central picture screen by flashing, so that the monitoring person at the central station immediately recognizes that there is a case of alarm at a bedside device with a certain bed number.

The alarm can also be communicated by the central station 83 via a central bus 132 to other bedside devices not giving an alarm. Here, then, a LED key lights up, e.g., as previously described. By pressing such a key, the central composite video signal CVC can be taken over on the picture screen of the oscilloscope of the respective device while its own display is turned off.

Figure 9:
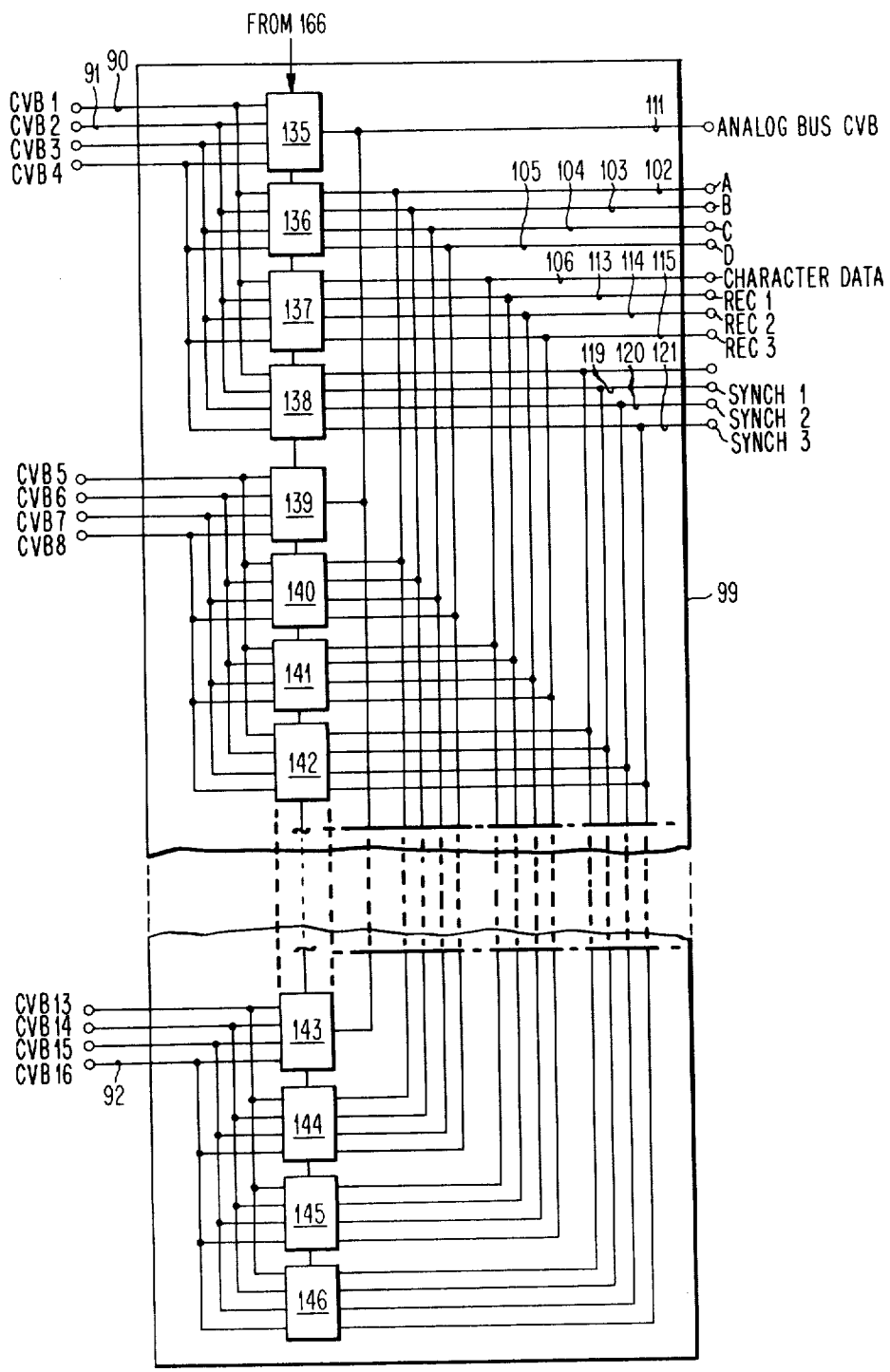
FIG. 9 is a central multiplexer, which is a component of the central unit in the star connection of FIG. 8.

FIG. 9 shows in more detail the internal basic construction of the multiplexer 99, as previously explained as to construction and mode of operation in conjunction with the star connection of FIG. 8. The distribution of the various signals in the multiplex operation over the different output lines is accomplished by the usual analog switches 135 to 146 in the interior of the multiplexer.

Figure 10:
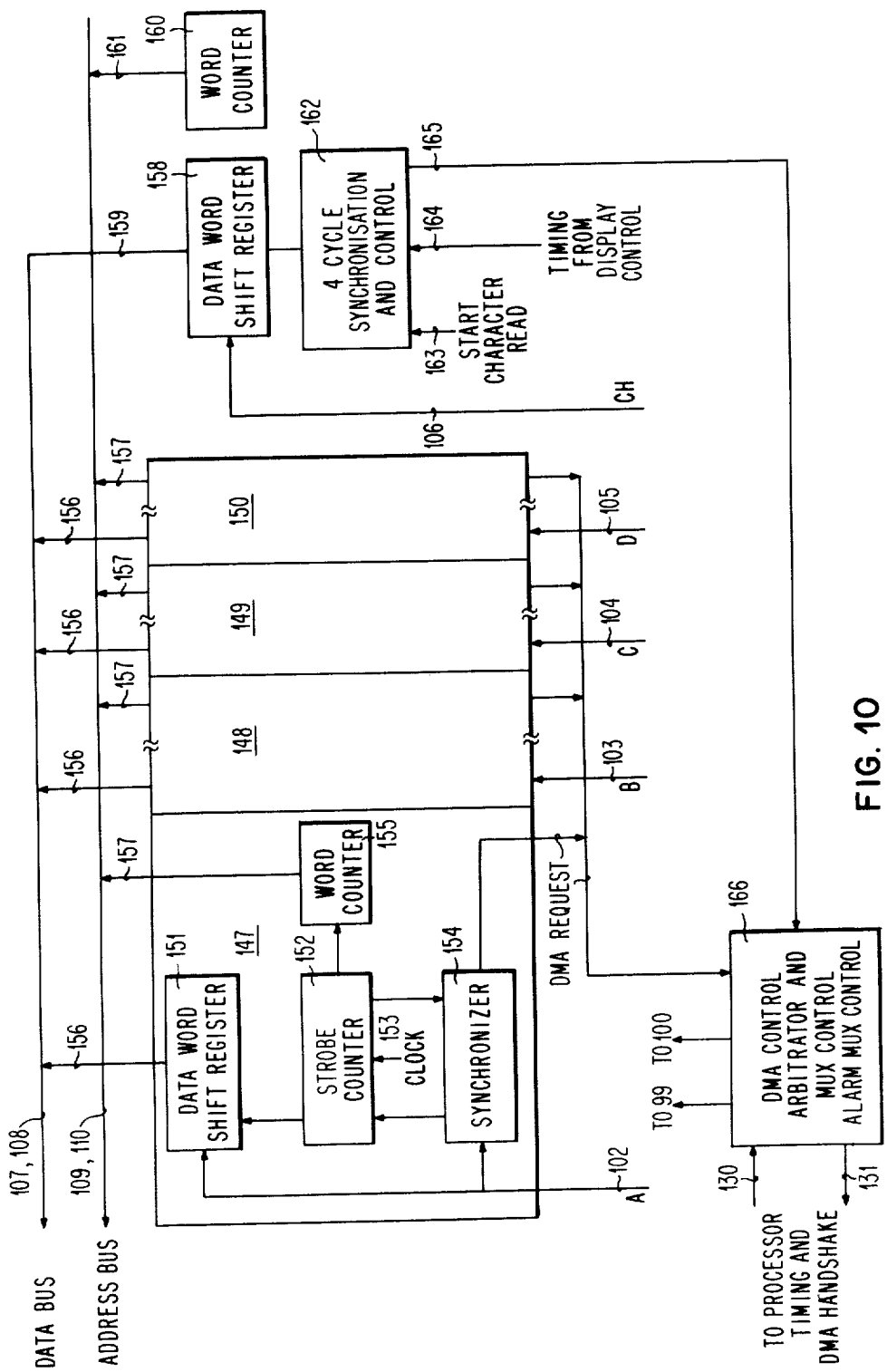
FIG. 10 is a control system for data and address control between the central multiplexer and a central image repeat memory, which control system is a component of the central unit of the star connection of FIG. 8.

FIG. 10 shows the internal construction of the control system 101 per FIG. 8 in the wiring between the multiplexer 99 on the one hand and the frame repeating memory 97 and central processor 98, on the other. The control system comprises, with respect to the location- and time-correct forwarding of the delayed data A to D, four separate blocks 147 to 150, each of which is in principle constructed in the interior as shown in detail for block 147. Each of the blocks 147 to 150 thus comproses a data word shift register 151, a strobe counter 152 for strobing the shift register, which contains a clock input 153, a synchronizer 154 for the counting clock pulse, and a word counter 155 for the addresses. The output data of the data shift register 151 go via an output 156 to the data buses 107, 108 for frame repeating memory 97 and central processor 98. The output addresses of the word counter 155 go correspondingly via an output 157 to the address buses 109, 110 for frame repeating memory and central processor.

The control system 101 comprises, in addition, for the forwarding of character addresses CH, a shift register 158 for data words with output 159 to the data buses 107, 108 and a word counter 160 with output 161 to the address buses 109, 110. Block 162 also comprises a synchronizing and control system (four cycle synchronization and control) with start input 163 for starting the reading of a character (start character read) and input 164 for the time pulse which controls the picture composition of the character (timing from display control, cf. again FIG. 6 in conjunction with FIG. 5). An output 165 leads to a control unit 166 (DMA control arbitrator and multiplexer control) which is in communication with the central processor via lines 130 and 131.

Figure 11:
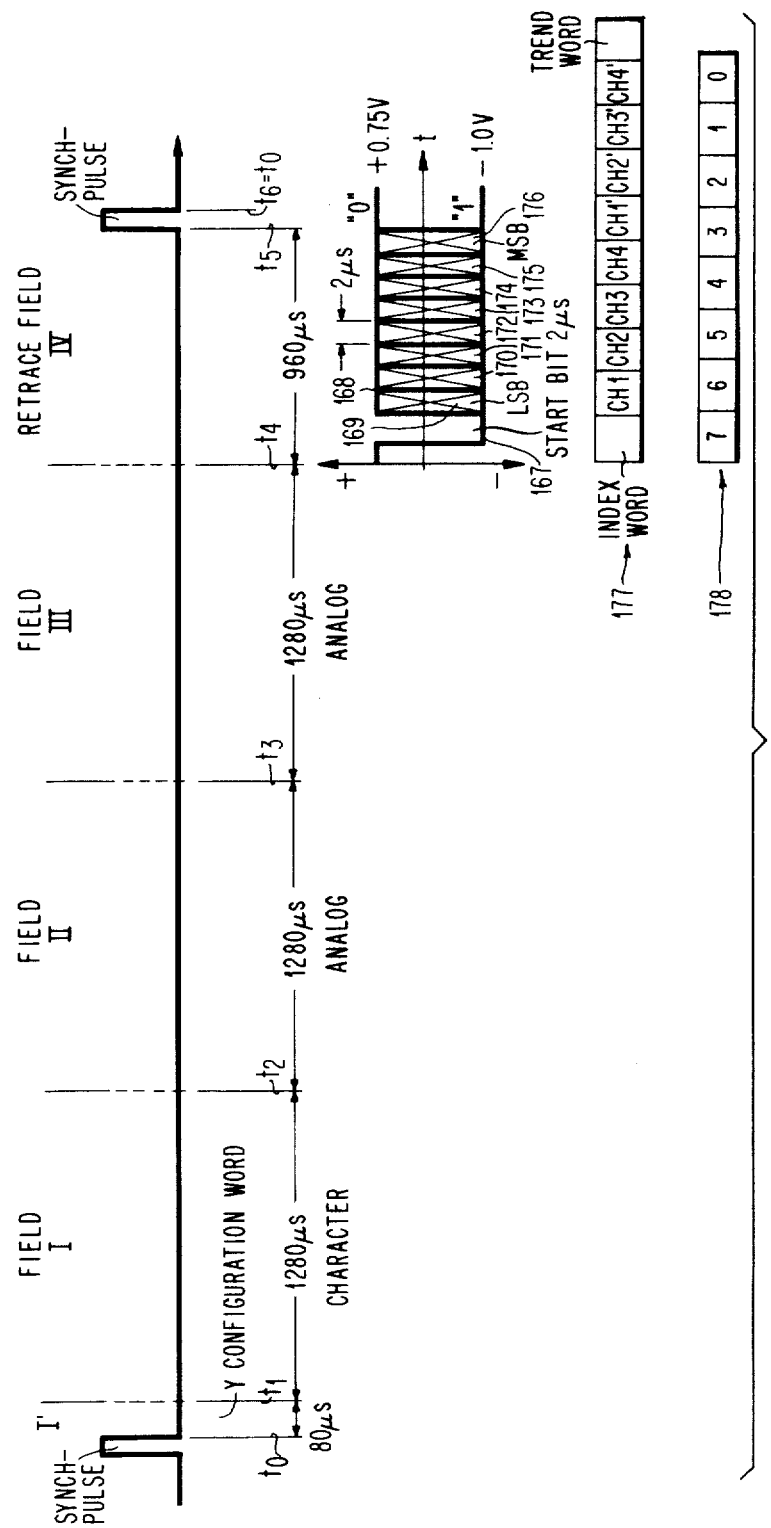
FIG. 11 is a time diagram according to FIG. 4, illustrating additionally a digital signal transmission in the retrace time of the x-deflection.

As previously mentioned, for the mixing of signal tracks there are used delayed data which occur in the respective retrace phases (time) of the x-deflection. Referring back to FIG. 4 the time span of this retrace phase is 960 μs, as is depicted once more at the top of FIG. 11. At variance with FIG. 4, however, there is entered in FIG. 11, below the previously described time diagram, a pulse timing which is set forth in purely schematic form the data transmission in Field IV during the retrace phase of the x-deflection. The data transmission is in digital form. As already shown in the y-configuration word of Phase I', so also in the digital signals of the retrace time IV, the state ZERO ("0") is documented by the appearance of the voltage level +0.75 V, and the state ONE ("1") by the appearance of the voltage level −1 V in the composite video signal. Now in the retrace phase IV, up to ten digital words can be transmitted, each comprising 8 bits. In retrace phase IV, except for the times of the transmission of digital words, a ZERO ("0") is conveyed, i.e., the composite video signal is on level +0.75 V. About 50 μs after start of the retrace phase, the transfer of digital word is begun. Each word to be transferred is inaugurated with a start bit 167, which is 2 μs long and which signals a ONE ("1"). After this start bit comes a word 168, which consists of 8 bits 169 to 176, each of which is again 2 μs long. The single bits 169 to 176 may show ZERO or ONE status, depending on the word content. In FIG. 11, these alternating possibilities between ZERO and ONE are indicated schematically by two diagonals in each bit. In each word the first bit is designated by LSB and the last bit by MSB, LSB meaning "Least Significant Bit" and MSB "Most Significant Bit". This establishes for each word the direction in which the bits of this word are to be read. Within the retrace phase IV of a total of 960 μs, therefore, up to ten such 8-bit words are transmitted, each new word being announced and initiated by a new start bit. Between the end of the last word of such a sequence and the end of the retrace phase there are moreover about 60 μs reserve time.

In FIG. 11, such a sequence of e.g. ten words of 8 bits each are indicated by the number 177. Each first word of such a sequence, which is always transmitted, is an index word. This index word, which in FIG. 11 is shown in detail in the bottom representation under number 178 broken down into its eight bits, gives information about flow data for the recording, as, e.g., about recording speed, the channel selection (channels CH1 to CH4, respectively CH1' to CH4'), the presence or absence of trend points, the existence of real time and-/or delayed data, etc. The first four words following the index word define delayed signal data for the four channels CH1, CH2, CH3, and CH4 and are entered in the word group 177 with this designation. At lowest signal transmission speed, normally only one oldest data occurs per retrace phase. At highest speed, however, up to two oldest data can occur. This last-named possibility takes into account a word group 177 by four additional words, which are marked in FIG. 11 by CH1', CH2', CH3', CH4'. If, therefore, a total of two delayed data occur per retrace phase, the respective pair is found in the word pairs CH1 and CH1', CH2 and CH2', etc. The tenth and last word of the word group 177 is lastly a word for a trend, if such a trend had previously been requested by a trend evaluator, in particular a trend recorder, via the index word.

Together there results the following scheme of a word group with e.g. ten words:

| | | |
|---|---|---|
| Word 1: | Index word | is always transmitted |
| Word 2: | CH1 | occupied at lowest occurrence rate |
| Word 3: | CH2 | 1 word/9.778 ms (12.5mm/s) and |
| Word 4: | CH3 | at highest occurrence rate |
| Word 5: | CH4 | 2 words/4.884 ms (50mm/s) |
| Word 6: | CH1' | not occupied except |
| Word 7: | CH2' | at highest occurrence rate |
| Word 8: | CH3' | of 2 words/4.884 ms |
| Word 9: | CH4'; | (50mm/s) |
| Word 10: | Trend point | transmitted only upon request by trend recorder |

The 8-bit index word is composed for example as follows:

| BIT 0 | | |
|---|---|---|
| 1 | | Transmission is valid |
| 0 | | Transmission is invalid |
| BITS 7 and 6 | | |
| BIT 7 | BIT 6 | |
| 0 | 0 | no data points transmitted |
| 0 | 1 | rate: 1 data point/channel/9.778ms |
| 1 | 0 | rate: 1 data point/channel/4.884ms |
| 1 | 1 | rate: 2 data points/channel/4.884ms |
| BITS 5 and 4 | | |

Bits 5 and 4 code a channel number per table below:

| BIT 5 | BIT 4 | | |
|---|---|---|---|
| 0 | 0 | top channel | Ch 1 |
| 0 | 1 | middle top channel | Ch 2 |
| 1 | 1 | middle bottom channel | Ch 3 |
| 1 | 1 | bottom channel | Ch 4 |

Bit 3 identifies whether a trend word for the next display channel is included in the transmission ("1" Trend word included) Bits 2 and 1 identify the mode of the data points; i.e., normally delayed data, but may be real-time data if the device has been stopped. See table below:

| BIT 2 | BIT 1 | |
|---|---|---|
| 0 | 0 | normal, all delayed data |
| 0 | 1 | channel 4 stopped/real time data (Transfer mode) |
| 1 | 0 | channel 4 in Cascade Mode |
| 1 | 1 | all channels stopped/real time data |
| Bit 0 = 1 | | unit turned on. If zero, the entire transmission is invalid |

As mentioned before, a trend word is transmitted only if the transmission had been requested. This request can come from a recorder associated with the bedside device. Or it may come via UART through a central recorder of the central station (cf. description of FIG. 5).

Figure 12:
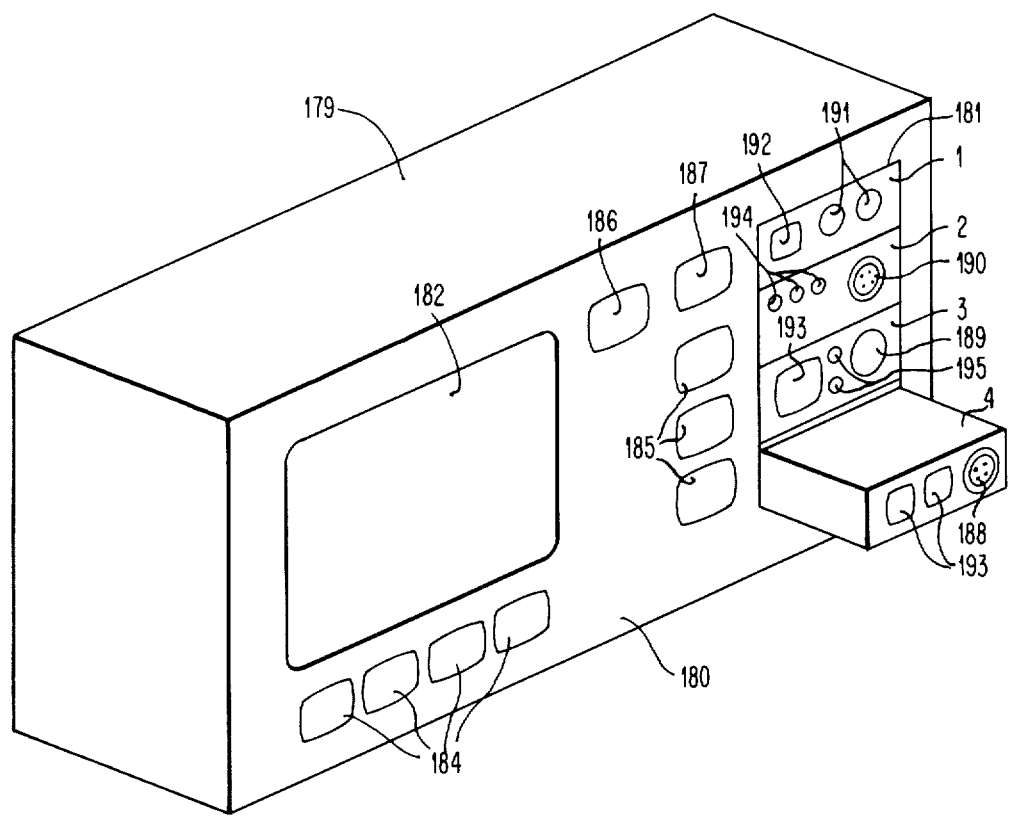
FIG. 12 is a perspective view of the basic construction of an electromedical monitoring device with four slide-in modules, which device is preferably used as a bedside unit.

FIG. 12 shows the basic mechanical set-up of an electromedical monitoring device with four slide-in modules, as used in connection with the invention, preferably as bedside device. The device comprises a device main frame housing 179 with the front panel 180. On the right side of the front panel is an opening for a recess in the interior of the device housing marked 181. Through this opening 181 a total of four slide-in modules, here numbered 1, 2, 3 and 4 in accordance with the basic diagram of FIG. 5, can be inserted in the recess. The device is equipped with an x, y, z oscilloscope, the picture screen of which is indicated by 182. The elements 184, 185 on the front panel are control and indicating elements, such as key switches, LED indicating fields, etc. Their arrangement is represented purely schematically. Element 186 indicates the previously described LED luminous key for indication and takeover of the foreign alarm. Element 187 marks, e.g., the reset key for an alarm in the device itself.

The devide shown in FIG. 12 is again specifically an electromedical devide. The slide-in modules 1 to 4 form part of the signal transmission system for physiological signals which are picked up on the patient's body by means of suitable electrodes. For this purpose, electrodes (not shown) are positioned on the patient's body and coupled with the respective slide-in over a signal cable (also not shown). For this purpose, the slide-in comprise jacks 188 to 191 for corresponding plugs of the signal cables. The remaining elements 192 to 195 are, again in purely schematic indication, data keys or LED indicator fields of the slide-in modules. In the example of FIG. 12, the bottom slide-in 4 is for example an EKG slide-in, the two central slide-ins are e.g. slide-ins for blood pressure and temperature measurement, and the top slide-in serves e.g. for $CO_2$ measurement. The device shown can be coupled with other similar devices to form a chain of a construction and mode of operation as shown in FIG. 7. Just as well the described device together with a corresponding number of additional devices can be assembled with a central station to form a star connection as shown in FIG. 8.

The order in which the individual slide-in modules 1 to 4 are arranged in the device of FIG. 12 is entirely arbitrary.

Figure 13:
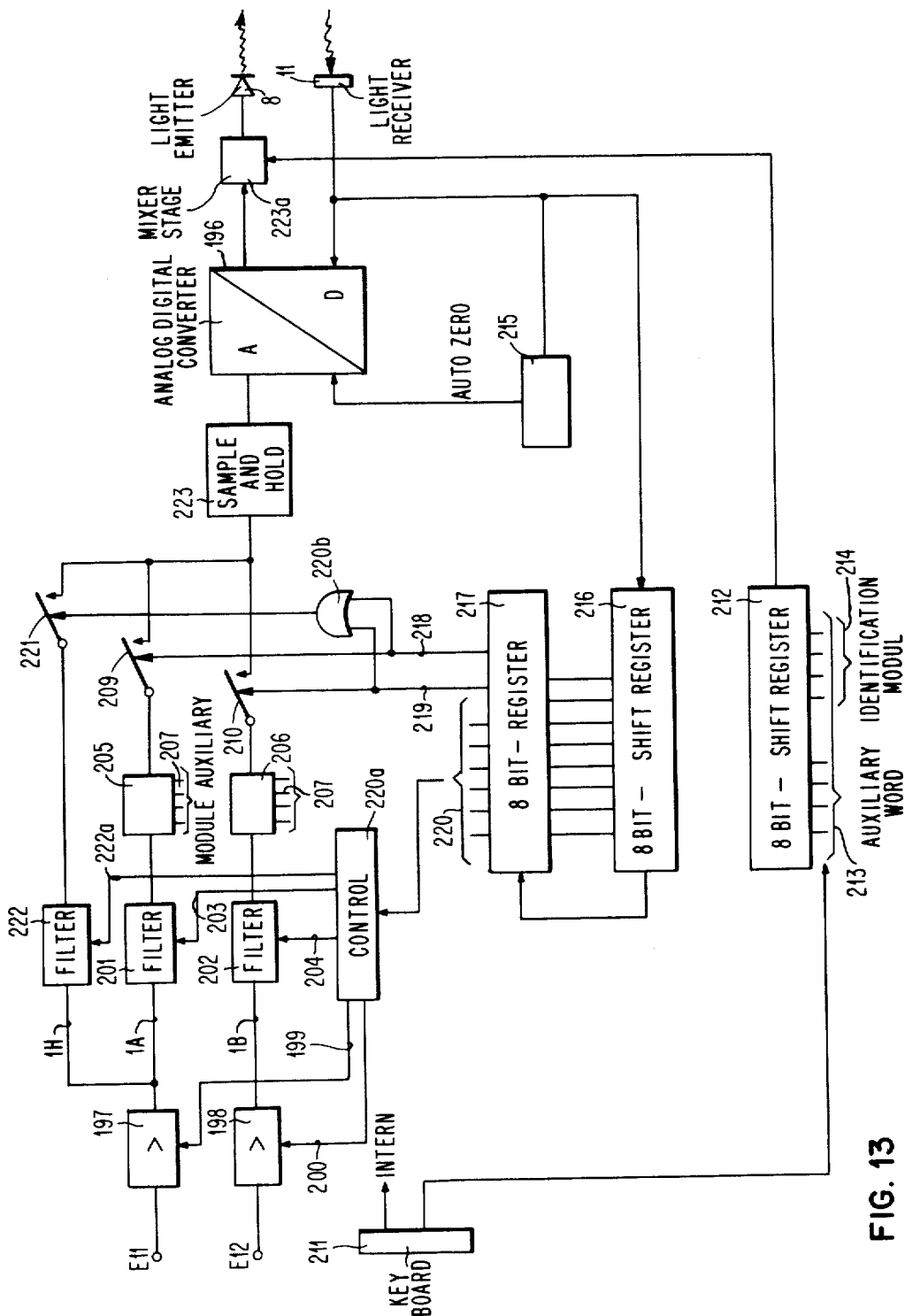
FIG. 13 is the basic internal circuitry of a slide-in module, in particular of a combined EKG/respiration module.
Figure 14:
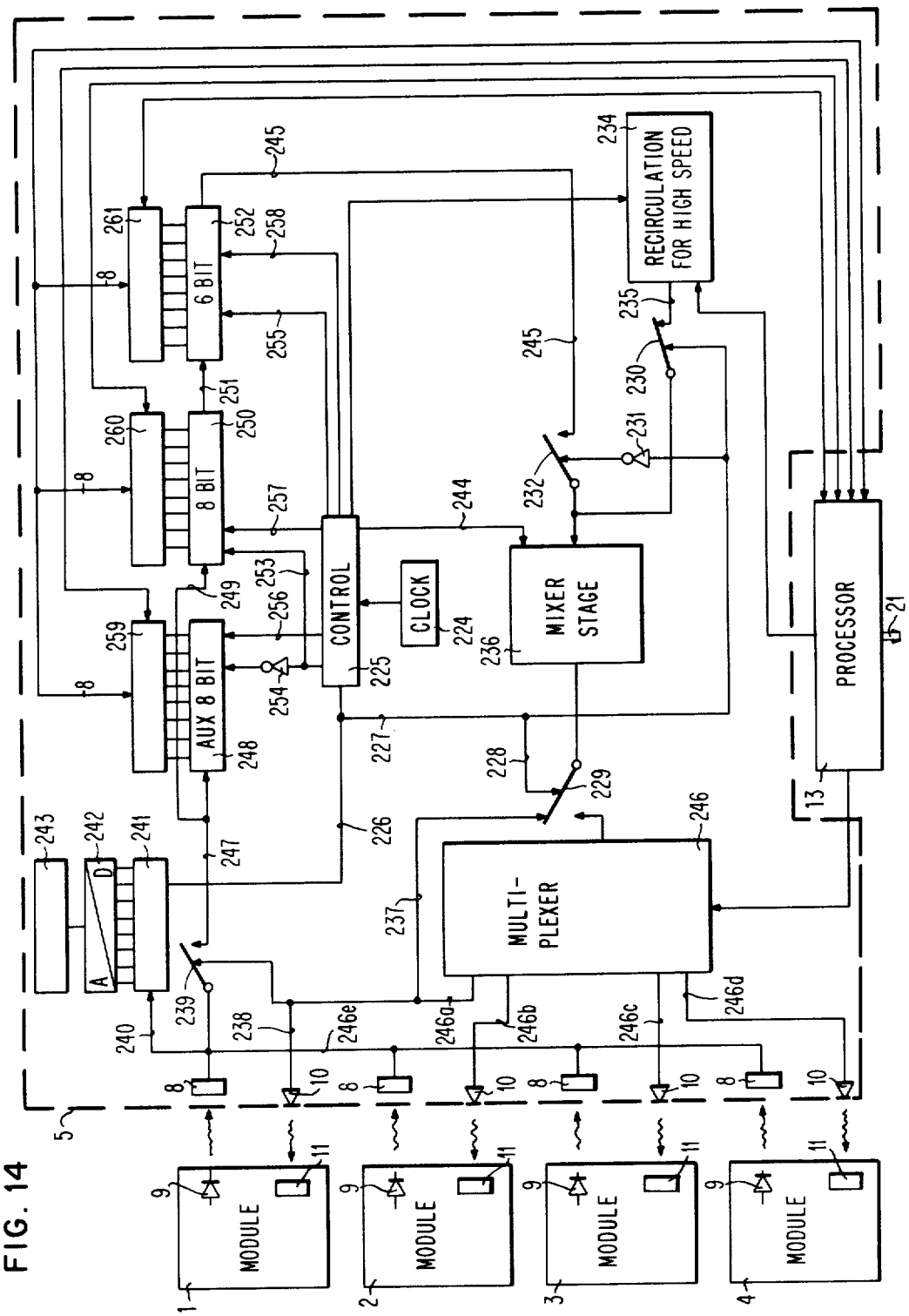
FIG. 14 is the basic internal circuitry of a control and coupling board for signal and energy coupling, which is provided opposite to the slide-in modules in the main device of a monitoring device.
Figure 15:
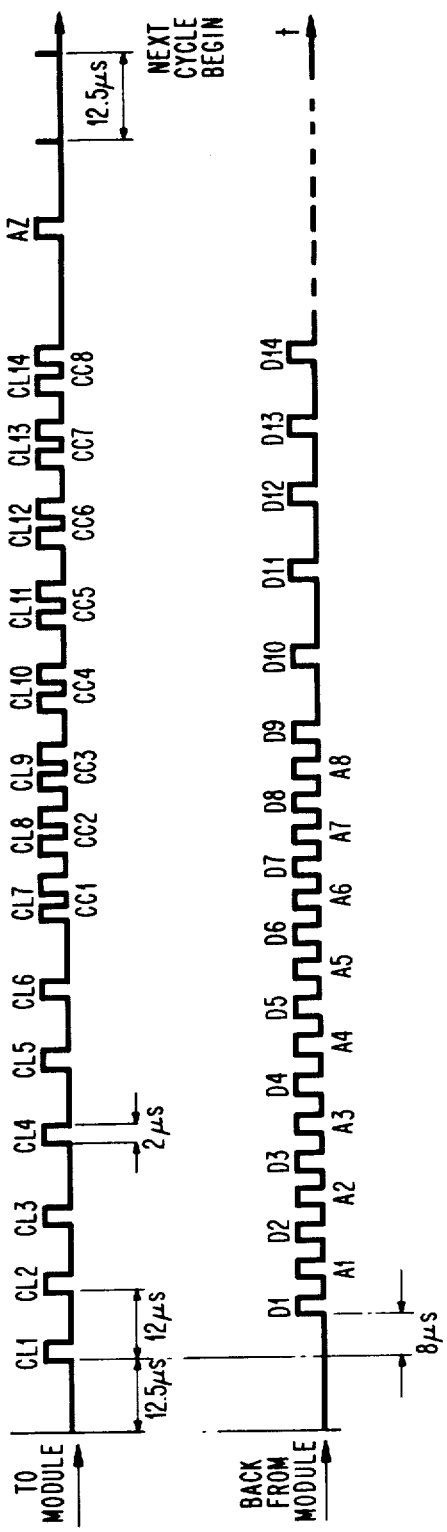
FIG. 15 shows pulse diagrams showing pulse trains, which are transmitted in one and the other direction between the slide-in modules and the main device.

This is ensured in simplest manner according to FIGS. 13 to 15 in that at least one analog-to-digital converter 196 per slide-in 1 to 4 is correlated with the preprocessing microprocessor in the device on the side of the slide-in modules 1 to 4 in signal transmission direction before each coupling point 8,9. Regardless of what kind the slide-in modules are and in what order or spatial correlation to each other the slide-in modules are plugged in to the bay of the device, the individual analog-to-digital converters 196 of all plugged-in modules 1 to 4 are now clocked for conversion according to a preset timing from the main frame circuits. The correlation of individual converted signal values to a module occurs in the processing section in simplest manner by an identification signal for each single module 1 to 4, which is transmitted in shared time together with the converted signal values.

In the total scheme of this mode of transmission, the analog-to-digital converter 196 of each slide-in module 1 to 4 are designed to be as inexpensive as possible and at the same time operate at maximum efficiency. According to the present embodiment of FIGS. 13 to 15, this is ensured in that analog-to-digital converters 196 are employed, which, at a relatively low given conversion rate per unit time with regard to the different frequencies of individual signals in the different frequency channels, are scanned with correspondingly different frequency. FIG. 13 shows as an example, in basic circuit diagram, the essential internal construction of an EKG slide-in with three channels 1H, 1A, 1B. Channel 1H is a maximum speed channel; this channel, which is instrumented only in the EKG slide-in, is scanned 2400 times per second. By this high scanning frequency, processes of an above average high frequency, e.g., arrhythmic events or pacemaker pulses, are picked up and indicated in the EKG. The maximum speed channel 1H thus may operate in connection with an additional arrhythmia processing section (e.g., arrhythmia computer). Channel 1A, however, is the main data channel for the EKG. It is scanned 400 times per second. Channel 1B may serve as a second data channel for another parameter. It is scanned only 200 times per second. What has been said for channels 1A and 1B applies similarly in principle also for the other three slide-in modules 2 to 4. These slide-in modules contain corresponding channels 2A, 3A, and 4A respectivey 2B, 3B, and 4B.

As has been indicated, all four slide-ins are similarly designed as far as channels A and B are concerned. As shown in FIG. 13, they all comprise the signal inputs E11 and E12. Each of these signal inputs is followed by a preamplifier 197 and 198. Each of the preamplifiers has a control input 199, 200 by which the gain can be regulated by control signal. The adjustment can be made with reference to bit combinations which together with a configuration word for the conversion are transmitted from the signal-processing section in the main frame to the respective module. The same also applies, e.g., to the pass band frequencies of frequency filters 201 and 202, which are adjustable via corresponding control inputs 203, 204 of the respective filter, likewise as a function of corresponding bit combinations in the conversion-configuration word. The filters 201 and 202 are followed by state signalers 205 and 206 which at outputs 207 and 208 by corresponding bit indicates the respective state of the module in the respective channel. The state signalers 205 and 206 function in a known manner, e.g., measuring members which ascertain whether the electrodes for the individual signals are correctly positioned on the patient's body and whether the signal pickup and transmission in the channels themselves is in order. These data, together with identification signals for the respective module, and e.g., also, together with further data which had been introduced, for example, over a bank of keys of a module are transmitted as an auxiliary word from the module toward the processing section of the device. In FIG. 13, the bank of keys of a module is schematically indicated by the number 211. For the transmission of the auxiliary word, an 8-bit shift register 212 is used, which on four inputs 213 of 1 bit receives auxiliary data from the signal transmitters 205 and 206 and possibly from the bank of keys 211. The four bits of the remaining four inputs 214 of shift register 212 formulate the identification signal for the respective module. These four inputs 214 for the identification signal are prewired differently for each module. The auxiliary word of the shift register 212 of each slide-in module, together with the digital data of the A/D converter 196, is transmitted via the sending diode 8 to the associated photo-receiver 9 in the signal processing section of the device. The signal train of digital data, sent into the device from the respective module 1 to 4, is represented in FIG. 15, bottom. Pulses D1 to D14 are the digital data of the A/D converter 196. They are shown with diagonal marks to indicate their value may be zero or one. The interpositioned eight pulses A1 to A8 are the auxiliary data; they form the auxiliary word and contain the identification signals for identification of the respective sending module. (They, similarly, may be zero or one.).

The pulse train which is transmitted from a light emitter 10 on the main frame side to a light receiver 11 on the side of the respective module 1 to 4, and which sets the conversion timing for the respective A/D converter 196, is indicated in FIG. 15, top. This pulse train comprises per conversion cycle a total of fourteen pulses CL1 to CL14. The interspersed pulses CC1 to CC8 and the 8 bits which serve as configuration word for adjustment of the filters and amplifiers on the basis of commands transmitted from the device side. These commands are generated by the respective microprocessor on the device side itself. They may be commands which, e.g., by key depression had first been introduced from the slide-in and been transmitted as constituents of the auxiliary word from the module to the device and had been returned from there to the slide-in after conversion in the respective microprocessor as a constituent of the configuration word. The slide-in modules themselves do not contain any active control elements, such as module-specific microprocessors or the like. A command input at the module via keys thus never acts directly on the module; rather, it is always processed via the microprocessor in the signal processing section of the device. Accordingly, each cycle of conversion pulses include corresponding pulses of a configuration word, by means of which commands can be carried out in the respective slide-in.

As has been mentioned, each conversion cycle contains a total of fourteen clock pulses for the corresponding fourteen conversions at the A/D converter 196. The clock pulses are each 2 μs long and the interval between each other is 12 μs. In each cycle the fourteenth clock pulse CL14 is followed after 24 μs by a last pulse AZ. This pulse AZ is an "Auto Zero Pulse" which, via a pulse forming member 215 (e.g., monoflop), automatically sets the A/D converter 196 to ZERO. Considering that each first clock pulse CL1 is generated only 12.5 μs after the start of a cycle and the respective cycle is ended only 12 μs after appearance of the AZ pulse, these results a total duration of a cycle of 204.5 μs. Another 12.5 μs after the end of a cycle, a new cycle begins, as indicated schematically in the pulse diagram of FIG. 15, top.

In the basic circuit diagram of FIG. 13, the occurring clock pulses CL1 to CL14 for the conversion timing go directly to the A/D converter 196. The eight pulses CC1 to CC8 of the configuration word, instead, are entered in an 8-bit shift register 216. The separating is accomplished by a separator circuit. But while the respective word of a cycle is being registered in shift register 216, the conversion clock of the preceding cycle is still running. The configuration word of the preceding cycle is contained in an 8-bit shift register 217. So, while a normal conversion cycle is still running, information for the next following cycle is already stored in the shift register 216. The respective module is thus already set for the requirements of the next following cycle although this cycle has not begun at all. By this design technique of advance storage of a configuration word with command data for a next following cycle, time is saved in the conversion as well. Each configuration word stored in shift register 216 is transferred to the second shift register 217 in direct parallel storage upon arrival of the last pulse CC8. The configuration word for the next following cycle is thus available at the output of the second shift register 217.

As has been mentioned before, the 8-bit shift register 217 supplies at six outputs 220 a total of six bits, setting information for, e.g., amplifiers and filters. The two remaining bits at outputs 218 and 219 are switching bits for the scanning switches 209 and 210 of channels 1A and 1B. In addition, by means of AND gate 220b, a third switching signal for a scan switch 221 in the high-speed channel 1H is generated, which channel 1H introduces a filter 222 for high-frequency components. The two bits of outputs 218 and 219 of shift register 218 thus define at what rate the individual channels 1H, 1A to 4A, 1B to 4B of the individual slide-in modules 1 to 4 are scanned. According to a preferred realization of the invention, the scanning rate over a period duration of 4880 μs is established with the following sequence:

| 1H, | 1A, | 1H, | 2A, | 1H, | 3A, | 1H, | 4A, | 1H, | 1B, | 1H, | 2B |
| 1H, | 1A, | 1H, | 2A, | 1H, | 3A, | 1H, | 4A, | 1H, | 3B, | 1H, | 4B |

The A/D converter 196 shown in FIG. 13 may in principle be constructed as described in U.S. Pat. No. 3,588,881. The member between the scan switches 209, 210, 221, and the A/D converter 196 is an ordinary sample and hold member.

FIG. 14 shows the basic internal circuitry of the analog-to-digital control and coupling aligned with the slide-ins for signal and energy coupling on the device side. By comparison with FIG. 5, the preprocessing microprocessor (Preprocessor) is again marked 13. Arrow 21 leads toward main memory 15 (shared memory).

The time base for the pulses of a conversion cycle is furnished by a clock pulse generator 224 (counter) which is synchronized by the preprocessing processor 13. The pulses of the clock generator enter a control unit 225. In this control unit the above described scanning cycle 1H, 1A, 1H, 2A, etc., takes place over appropriate pulse switches. Each clock pulse for 1H goes to a clock line 226 and to a clock line 227. The clock pulse of line 226 controls a shift register 241 of a high-speed (wide bandwidth) analog output.

In line 227, instead, the same clock pulse controls a switch 229 into the switching position shown. At the same time a switch 230 is closed and via an inverting member 231 a switch 232 is opened. With each clock pulse for 1H there is generated via a control line 223 an enabling signal for a recirculation register 234 (recirculation register for high speed) in which conversion pulses 1H are continuously in circulation. The call signal brings about the delivery of a pulse 1H at the output 235 of recirculation register 234. Thence pulse 1H passes via the then closed switch 230 to a mixer stage 236 which forwards it via switch 229 to line 237 and thence via line 238 to the sending diode 10 of the transmitting channel for the top slide-in module 1. The emitting diode 10 sends pulse 1H toward photo-receiver 11 in module 1, which then forwards it as 1H scanning pulse on the one hand to the A/D converter 196, and on the other, to the formation of the shift registers 216, 217. Pulse 1H opens moreover a switch 239. Thereby scanning values of the 1H channel which at that moment are being supplied by the A/D converter of module 1 are conducted only to the shift register 241 of a high speed (wide bandwidth) analog output generator 241 to 243. From this shift register 241 the respective 1H value passes to a D/A converter 242, which reconverts it to its analog value. The analog value can be placed on a recorder 243. The result in then an analog signal curve giving information about events in the EKG of above normal high frequency.

The mixer stage 236 is a pulse mixer in which there are admixed to the pulses 1H, in the given sequence, the remaining scanning pulses for the channels 1A to 4A and 1B to 4B via a line 244. To these pulses are added finally, also, via a line 245, the eight pulses CC1 to CC8 of the configuration word which is to be retransmitted into the respective module. The admixing occurs over the closed switch 232. The pulse train thus mixed is supplied, via switch 229 controlled into the position shown in dashed lines alternate to the clock pulses 1H position, to a multiplexer 246. This multiplexer, controlled by the preprocessing processing 13, then clocks the transmitting diodes 10 via lines 246a, 246b, 246c, and 246d. By them light pulses are sent in the desired sequence to the photo-receivers 11 on the side of the slide-in modules 1 to 4, whence they pass as conversion clock to the A/D converters 196 or respectively as configuration word to the shift registers 216, 217.

In the case of FIG. 14, the high speed channel for the 1H scanning has assigned to it a fixed slide-in in top position. In the practice, however, relatively high-frequency events occur at most in conjunction with EKG measurement. Thus a high speed signal is practically received only when the EKG module is plugged in the first position. If this position is occupied, instead, by a slide-in for signals of lower frequency, the high speed scanning 1H runs idle. If high speed scanning is wanted, the EKG slide-in must be plugged in position 1. But all other positions are selectable at will.

As is illustrated in FIG. 15, bottom, the device receives from the respective module 1 to 4 data D1 to D14 together with an auxiliary word A1 to A8. This auxiliary word contains also the identification signal for the respective slide-in module. Now, according to FIG. 14, all pulses received by the photo-receivers 8 on the device side are sent to a pulse line 246e, whence they pass via switch 239, which is always closed when such pulses occur, to line 247. Thence they are forwarded, on the one hand, to the input of a first 8-bit shift register 248. On the other hand, they pass via a line 249 also to the input of a second 8-bit shift register 250. Overflow pulses leaving the second shift register 250 are clocked via a line 251 into a third shift register 252, which is specifically a 6-bit shift register.

The shift registers 248, 250 and 252 are clocked by the control unit via clock lines 253, 254, and 255. The shift registers 250 and 252 run in push-pull to shift register 248, which is activated via an inverting member 254. Lines 256, 257, and 258 are enable control lines for the respective shift register. The push-pull at shift register 248 has the result that there are registered by this register only those data of the occurring pulse train which occur in pauses of the measured value data D1 to D4. Such data, however, are data A1 to A8 of the auxiliary word. And so the 8-bit shift register 248 picks up the data of the auxiliary word. As soon as the first eight single data have occured, overflow to the 6-bit shift register 252 takes place. At the end of each conversion cycle, the 8-bit shift register 248 contains the auxiliary word, while in the 8-bit register 250 there are stored the measured data D14 to D7 and in the 6-bit register 252 the measured data D6 to D1. The stored data can now be transferred in groups by polling systems (latches) 259, 260, and 261 to the preprocessing processor. Thence, they can be sent to the main memory via the shared memory and be transferred to the main processor for further processing.

Figure 16:
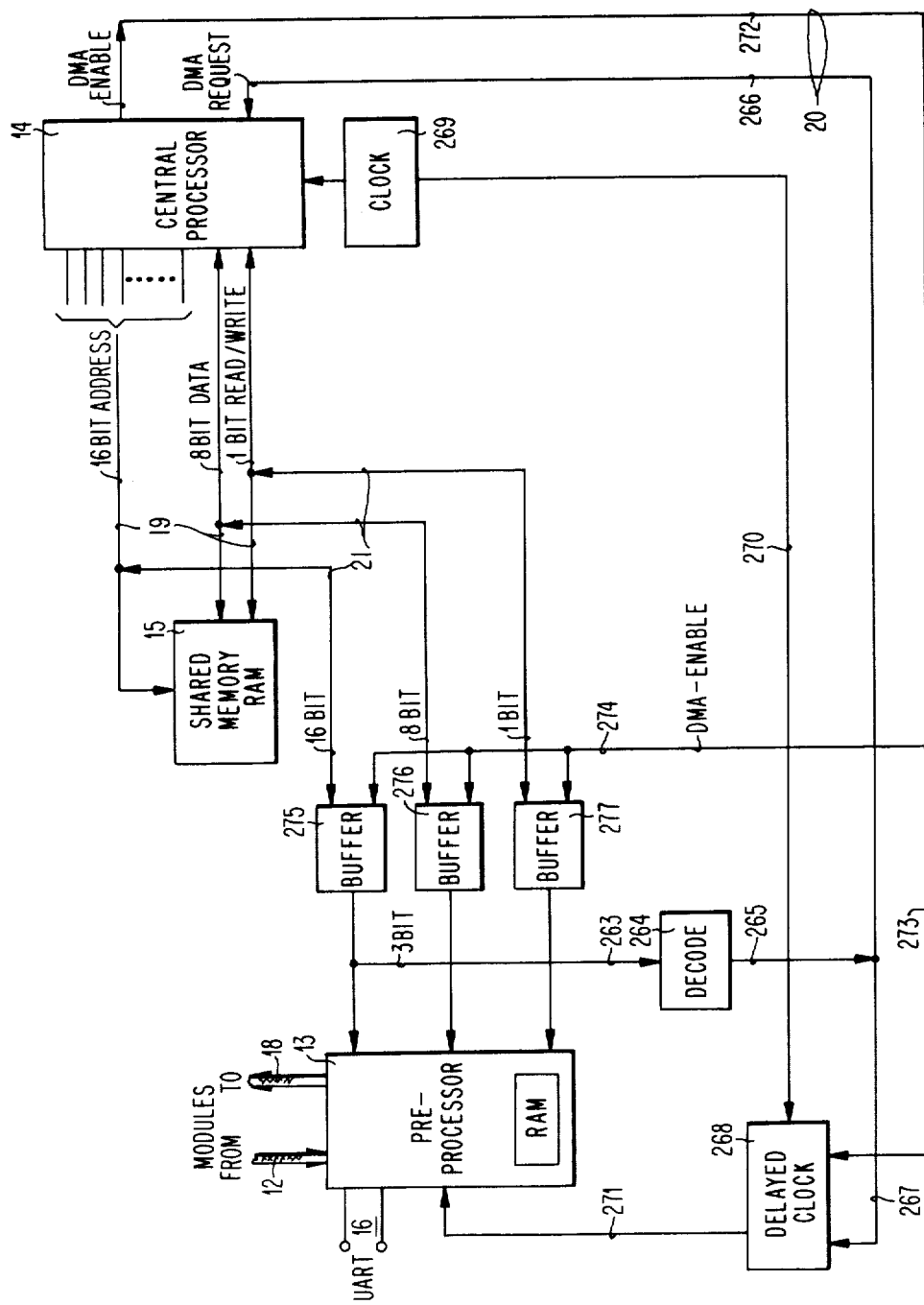
FIG. 16 is a circuit diagram illustrating the interaction between a preprocessing microprocessor (preprocessor), a main memory (shared memory), and a central microprocessor (central processor) of a monitoring device according to FIG. 5.

FIG. 16 shows the interaction between preprocessor, shared memory and central processor of a device according to FIG. 5 in detailed basic circuit diagram.

As has been mentioned at the beginning, the preprocessor 13 is not DMA capable, whereas the central microprocessor 14 is DMA capable, i.e., this processor is in fixed access correlation to the main (shared) memory 15. Now, by a special circuit design the preprocessor 13 is prepared so that it becomes DMA capable. The circuit operates as follows.

At certain intervals of time the preprocessor 13 issues a DMA request to the central processor 14. This is done in that there appears at the output of the preprocessor 13 a certain address. In the present embodiment of FIG. 16 this address consists e.g. of three binary ones. This address passes via an address line 263 to a decoder 264. This decoder 264 recognizes the selected address whenever it occurs. Thereupon it generates at its output 265 a DMA request pulse. This pulse then passes via a first branch line 266 to the central microprocessor 14. Simultaneously, it is sent via a second branch line 267 to a delay member 268.

The DAM request pulse arriving at the central microprocessor 14 initiates a response there. The central processor 14 completes those operations which it had started before arrival of the DMA request and had not yet completed. Thus, when a DMA request arrives, the central microprocessor is not turned off immediately; some time passes before its disconnection (all output buffers of the central processor occupy a high-ohm resistance value). During this time span, while the central processor 14 is still in communication with the main memory 15, it must be ensured that the preprocessor 13 remains disconnected from access to the main memory 15.

This is done in simplest manner by the clock delay member 268. This delay member is a frequency demultiplier which reduces the clock frequency at which the preprocessor 13 is clocked in the normal state to a much lower value compared with the normal value. In the present embodiment, the normal value of the clock frequency is about 4 MHZ, representing a pulse interval of the clock pulses of 0.25 μs. When the clock delay member 268 is activated by the DMA pulse, it reduces the clock frequency to a value of about 0.333 MHZ. The interval between clock pulses is then about 3 μs.

The normal value of the clock frequency is given by a clock pulse generator 269, which furnishes the timing both for the central processor 14 and for the preprocessor 13. The pulses of the clock pulse generator 269 pass via line 270 to the frequency demultiplier 268. As long as the latter is switched to normal operation, the clock pulses of line 270 are passed undelayed via line 271 to the preprocessor 13 as operating clock pulses. But if a DMA request pulse is applied at the frequency demultiplier, the cycle described above occurs, in which the clock frequency of the pulses of line 270 is reduced in the manner described. Then only clock pulses of reduced frequency reach the preprocessor 13 via line 271. Preprocessor 13 is thereby delayed in its cycle; it is not yet ready for communication despite the DMA request having been issued. This situation changes the moment an acknowledgement signal is given by the central processor 14, whereby the central processor confirms that its own communication with the main memory 15 is terminated.

In FIG. 16, this acknowledgement signal appears as DMA-enable signal in the output line 272 of the central processor. Thence it is applied via a line branch 273 on the one hand to the clock delay member 268; on the other hand, it is sent simultaneously via a second line branch 274 to the output buffers 275, 276, and 277 of preprocessor 13. The enable signal causes the clock delay member 268 to be reset to its normal operating position. From that time on member 268 again permits clock pulses of generator 269 of normal frequency to pass to preprocessor 13 via the output line 271. Thus, preprocessor 13 again operates at its normal operating frequency. In addition, the DMA enable signal switches the previously high-ohm output buffers 275 to 277 of preprocessor 13 to forward conduction. All prerequisites of the DMA capability are thus fulfilled; preprocessor 13 can now enter into communication with the main memory 15 via line 21.

Thereby, then, a preprocessor which in itself is not DMA capable is connected as if it were DMA capable. The described circuit works with simplest technical means; additional software support of the preprocessor for the generation of the DMA request is not necessary. All important functions are carried out without the preprocessor itself being aware of them.

In signal reproduction by means of dynamic repeat memories there are, as is known, two possibilities of signal representation.

The first possibility involves one in which oldest information in the memory is continuously being replaced by latest information. On the picture screen of the display device this leads to a continuous signal train of oldest and latest measured values. This display mode, which produces migrating signal trains, is commonly referred to as "paper mode".

A second display mode is the so-called "fixed mode". Here signal information once entered in the memory circulates cyclically, without oldest information being replaced by latest information. There results on the picture screen of the display device a frozen-in signal image. How to be able to recognize on the continuously circling frozen-in image where beginning and end are in the signal train, it is common practice when adopting the "fixed mode" to fade into the plot a vertical bar which together with the information moves over the picture screen continuously. The moving vertical bar indicates the boundary between new and old signal information in the memory. It thus shows where the circulating signal has its beginning and where it ends.

Figure 17:
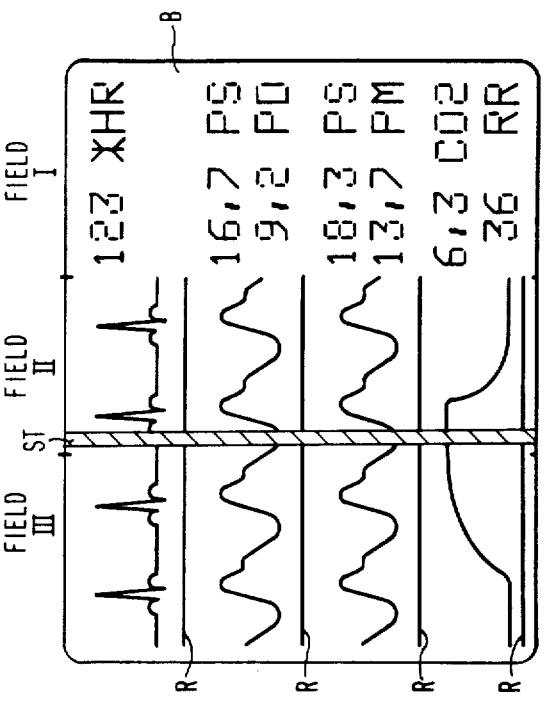
FIG. 17 is a display showing the signal and character representation of FIG. 2 with a moving vertical blanking bar as a limit between new and old signal information in fixed mode operation.

FIG. 17 shows the signal and character display of FIG. 2 in "fixed mode" with moving vertical bar ST. The generation of a vertical bar for "fixed mode" presents no difficulties for the normal known application, that is, that the information issued cyclically by the picture repeat memory is put directly on the own disply device.

Problems arise, however, when the "fixed mode" is applied to composite video display. Direct transmission of a blanking pulse, which is the basis for bar indication, between individual devices of a chain or star configuration is not possible.

Figure 18:
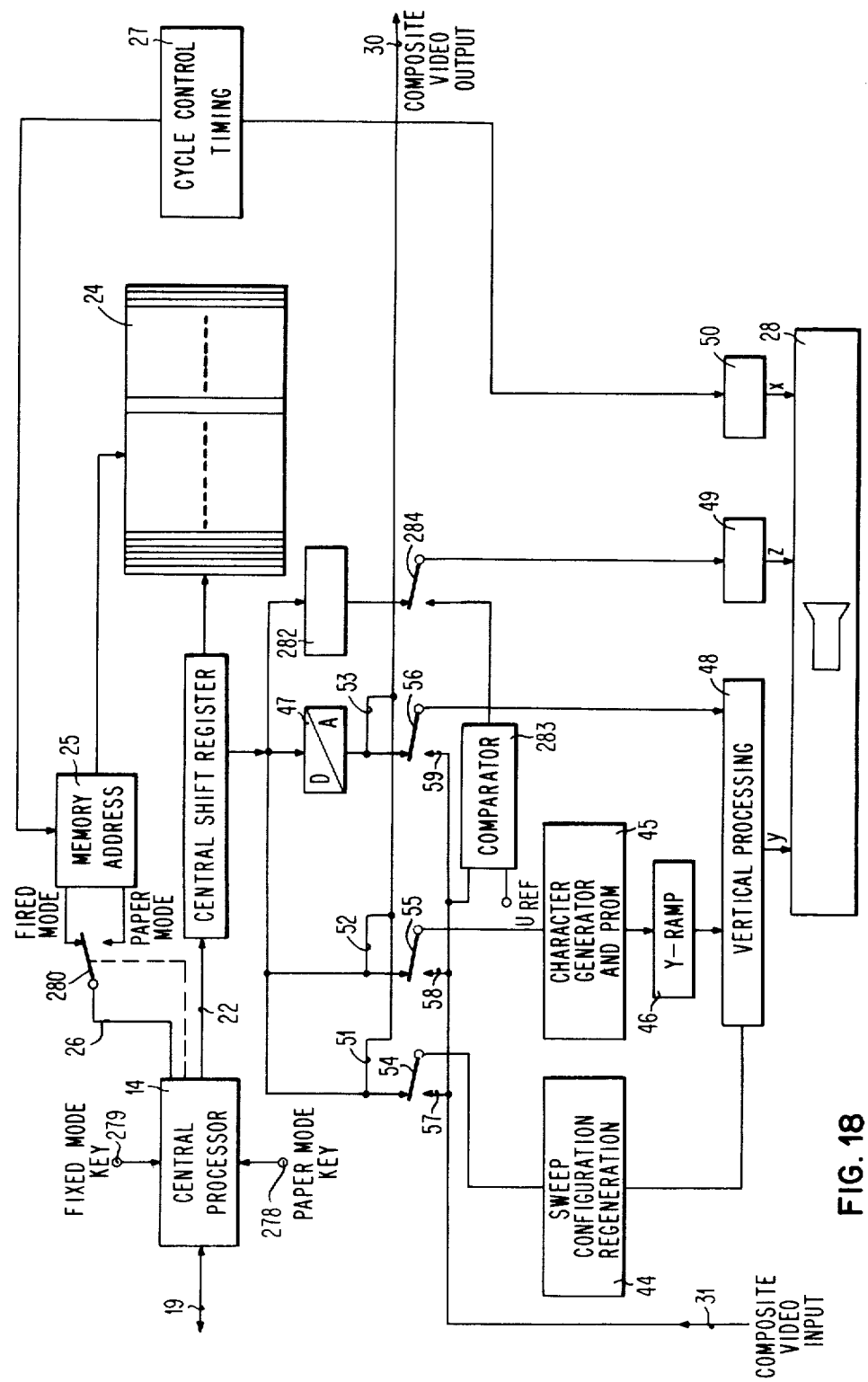
FIG. 18 is a basic circuit diagram for producing a vertical blanking bar according to FIG. 17.

FIG. 18 shows a principle how in an especially ingenious manner and without great additional circuitry expense also for composite video the use of bar display is possible, so that here, too, a selective display in "paper mode" or in "fixed mode" can be effected. The basic circuit diagram of FIG. 18 is very similar to that of FIG. 6. It is merely supplemented by those structural elements which are necessary for bar generation. Accordingly, the device of the diagram of FIG. 18 has two selector keys 278 and 279. Key 278 selects the "paper mode", key 279, the "fixed mode".

The pushing of a selector key 278 or 279 is registered by the central microprocessor 14 as selection of a certain mode of operation.

Normally switch 280 at the input of the address computer 25 is in the "paper mode" position. By actuation of key 278 the "paper mode" of operation is already preselected. The circuit operates as has been described in the preceding passages.

But if the selector key 279 is pushed, the central microprocessor 14 generates a switching signal for switch 280. Thus switch 280 is controlled into the "fixed mode" position.

This, as distinguished from "paper mode", results in the following cycle.

The accesss of new measured value information to the picture repeat memory 24 is not transmitted by the central microprocessor 14. The address counter 25, however, generates an address strip of, e.g., a total of 16×8 ONES. This address strip is entered by the address counter at that point in the picture repeat memory 24 at which oldest signal information in the memory is adjacent to latest (or newest) signal information. The address strip 281 of binary ONES thus differentiates the signal beginning in the memory from the signal end.

The address strip 281 of 16×8 ONES is now passed to the display device together with the continuously circulating stored signal information by the frame repeat memory 24, cyclically, via the central shift register 23. The ONES reach a logic gate 282 which precedes the z-unblanking generator of the x,y,z oscilloscope. The logic gate recognizes the existence of an address strip of ONES; it thereupon generates during the time span of occurrence of ONES a blanking signal for the z-unblanking generator 49 and supplies it to the latter via switch 284, which is in the position shown. During the time span of the blanking signal, therefore, the unblanking generator 49 remains switched off.

Each address strip 281 of ONES given out by the picture repeat memory 24 via shift register 23 goes simultaneously also to the input of the D/A converter 47. Thereupon the D/A converter 47 generates an output pulse, whose amplitude is much higher, because of the input information consisting only of ONES, than normal occurring signal amplitudes. This high-amplitude output pulse reaches the vertical deflection system 48 of oscilloscope 28. It there leads to an overcontrol. The electron beam of the oscilloscope is deflected very quickly and very far over the picture screen. Because of the very rapid beam deflection, the flanks of the pulse are not visible. The simultaneously arriving blanking pulse leads to the blanking in the limits of the deflection pulse. Thus, a dark strip for "fixed mode" becomes visible on the picture screen of the oscilloscope. This dark strip moves together with the continuously circulating signal information of the frozen-in image over the picture screen of the oscilloscope. Thus, an unambiguous visual expression is always possible as to where the beginning of the reproduced signals is located just then in the migrating picture and where the end.

The output pulse of very high amplitude occurring at the output of the D/A converter 47 is supplied, not only to the device-specific oscilloscope, but simultaneously also via the line connection 53, as component of the normal Composite Video signal, to the Composite Video Output 30 of the device. Thence, it goes to the Composite Video bus, if output 30 is connected to the bus.

As to the receiving section of a device, there are the following modification is provided.

In the receiving section, a comparator 283 is connected at line 59 which leads from the Composite Video Input 31 to switch 56 for the analog signal. This comparator has a reference voltage input, at which a reference voltage $V_{ref}$ is applied. If any device is switched to "fixed mode" and is to receive Composite Video signals of another device also operating in "fixed mode", the Composite Video Output of the sending device and the Composite Video Input of the receiving devide are interconnected. In chain connection of the devices, this can be done via the common Composite Video Bus or, in star connection of the devices, via the Central Composite Video Bus of the central station.

The receiving device now receives a Composite Video signal which contains in the analog section an output pulse of high amplitude as strip signal. The appearance of the high-amplitude pulse is recognized by comparator 283 as a threshold-exceeding event. Thereupon comparator 283 generates during the time span of the threshold excess an output signal. This output signal now serves specifically as blanking signal for the unblanking generator 49. It is supplied to the unblanking generator 49 via switch 284 now controlled into the position shown in broken lines. The unblanking generator 49 again causes beam blanking during occurrence of the remote origin blanking of the strip pulse. On the picture screen of the receiving device there now appears the "fixed mode" signal picture of the remote transmitting device with vertical blanking bar as boundary indication for signal beginning and signal end.

FIGS. 1 to 18 describe only a preferred embodiment of the invention. It is understood that the invention is not limited to this embodiment, but that there are any desired modifications of the embodiment which all are to be included under the protection of the invention.

What is claimed is:

1. An apparatus for processing digital signals, containing a microprocessor system, said microprocessor system comprising in combination:
    (a) a first processor which is DMA-capable,
    (b) a second processor which is not DMA-capable;
    (c) a main memory;
    (d) first connecting means associated with said first processor for connecting said first processor with said main memory via a first communication path;
    (e) second connecting means associated with said second processor for connecting said second processor with said main memory via a second communication path;
    (f) an input for said first processor for receiving an DMA request;
    (g) means associated with said second processor for issuing a DMA request at certain time intervals to said input for DMA request of said first processor;
    (h) means associated with said first processor for initiating the first processor's current operations such that those operations that the first processor had started before the arrival of the DMA request of said second processor and had not yet completed are now completed; and
    (i) means associated with said first processor for producing a signal when the first processor has completed its current operations, said signal controlling said first connecting means associated with said first processor and said second connecting means associated with said second processor to cut off said first communication path between first processor and main memory and instead close the second communication path between said second processor and said main memory.

2. The apparatus according to claim 1, wherein said second processor comprises a memory and an output for memory data read out in the normal read and write cycle, said output comprising an address line, and wherein said means for issuing a DMA request comprises a certain memory address in said memory of said second processor, said address forming the DMA request, and further comprises a DMA request decoder connected with said address line for recognizing the appearance of a DMA request in said address line.

3. The apparatus according to claim 2, wherein the certain memory address forming an DMA request, consists of three binary ONES.

4. The apparatus according to claim 1, wherein said second processor comprises a clock input for a clock frequency delivered by a clock pulse generator and wherein said second connecting means for connecting said second processor with said main memory comprise means controllable by the issue of a DMA request of said preprocessor and by the signal produced by said central processor, for reducing the block frequency of said clock pulse generator with respect to the second processor from a normal value to a lower value when a DMA request is issued by the second processor and for resetting said clock frequency from said lower value to said normal value when said signal of said first processor appears such that due to the lower frequency value the second processor is cut off from its connection with the main memory as long as the first processor has not yet completed its current operations.

5. The apparatus according to claim 4, wherein said means for reducing the clock frequency comprise a frequency reducer in the connection between said clock input of said second processor and said clock frequency generator, which frequency reducer is triggered by an issued DMA request and reset by said signal of said first processor.

6. The apparatus according to claim 4, wherein said normal value of said clock frequency is about 4 MHZ.

7. The apparatus according to claim 4, wherein said lower value of said clock frequency is about 0.333 MHZ.

8. The apparatus according to claim 4, wherein said connecting means for connecting said second processor and said main memory further comprising buffers at the outputs of said second processor and controllable by said signal of said first processor, which buffers are switched from a non conducting value to a forward value when said signal of said first processor appears.

9. The apparatus according to claim 1, wherein said first connecting means for connecting said first processor with said main memory comprise output-buffer incorporated in said first processor and controllable by said signal of said first processor such that the output buffer is switched to a high-ohmic resistance value when said signal of said first processor appears.

10. The apparatus according to claim 1, wherein said signal of said first processor comprises a DMA enable signal.

11. The apparatus according to claim 1, wherein said first processor is a central processor.

12. The apparatus according to claim 1, wherein said second processor is a preprocessor.

* * * * *